(12) United States Patent
Ganesh et al.

(10) Patent No.: US 9,428,478 B2
(45) Date of Patent: Aug. 30, 2016

(54) PIPERAZINE DERIVATIVES, COMPOSITIONS, AND USES RELATED THERETO

(75) Inventors: Thota Ganesh, Alpharetta, GA (US); Aiming Sun, Atlanta, GA (US); Susane M. Smith, Acworth, GA (US); John David Lambeth, Decatur, GA (US)

(73) Assignee: Emory University, Atlanta, GA (US)

(*) Notice: Subject to any disclaimer, the term of this patent is extended or adjusted under 35 U.S.C. 154(b) by 0 days.

(21) Appl. No.: 14/123,877

(22) PCT Filed: Jun. 12, 2012

(86) PCT No.: PCT/US2012/041988
§ 371 (c)(1),
(2), (4) Date: Mar. 24, 2014

(87) PCT Pub. No.: WO2012/173952
PCT Pub. Date: Dec. 20, 2012

(65) Prior Publication Data
US 2014/0194422 A1    Jul. 10, 2014

Related U.S. Application Data

(60) Provisional application No. 61/496,161, filed on Jun. 13, 2011.

(51) Int. Cl.
| | | |
|---|---|---|
| C07D 209/18 | (2006.01) | |
| C07D 401/12 | (2006.01) | |
| C07D 413/06 | (2006.01) | |
| A61K 31/496 | (2006.01) | |
| A61K 31/5377 | (2006.01) | |
| C07D 239/42 | (2006.01) | |
| C07D 307/14 | (2006.01) | |
| C07D 211/58 | (2006.01) | |
| C07D 239/90 | (2006.01) | |
| C07D 241/08 | (2006.01) | |
| C07D 295/185 | (2006.01) | |
| C07D 403/04 | (2006.01) | |
| C07D 241/50 | (2006.01) | |
| C07D 215/48 | (2006.01) | |
| C07D 235/24 | (2006.01) | |
| C07D 241/24 | (2006.01) | |
| A61K 31/498 | (2006.01) | |
| A61K 31/517 | (2006.01) | |

(52) U.S. Cl.
CPC .......... *C07D 307/14* (2013.01); *A61K 31/496* (2013.01); *C07D 209/18* (2013.01); *C07D 211/58* (2013.01); *C07D 239/42* (2013.01); *C07D 239/90* (2013.01); *C07D 241/08* (2013.01); *C07D 241/50* (2013.01); *C07D 295/185* (2013.01); *C07D 403/04* (2013.01)

(58) Field of Classification Search
None
See application file for complete search history.

(56) References Cited

U.S. PATENT DOCUMENTS

| | | | |
|---|---|---|---|
| 2,535,971 A | 12/1950 | Turner | |
| 4,988,698 A | 1/1991 | Kato et al. | |
| 7,968,746 B2 | 6/2011 | Jankowski et al. | |
| 8,389,518 B2 | 3/2013 | Page et al. | |
| 2009/0118257 A1 | 5/2009 | Jankowski | |
| 2009/0275555 A1* | 11/2009 | Ronzoni et al. | ......... 514/210.18 |
| 2013/0225612 A1 | 8/2013 | Lambeth et al. | |

FOREIGN PATENT DOCUMENTS

| | | |
|---|---|---|
| AU | 2006230674 | 11/2006 |
| WO | 2004035556 | 4/2004 |
| WO | 2005009947 | 2/2005 |
| WO | 2006086445 | 8/2006 |
| WO | 2008002674 | 1/2008 |
| WO | 2011002067 | 6/2011 |

OTHER PUBLICATIONS

"Burger's Medicinal Chemistry",edited by Manfred E. Wolff, 5th Ed. Part 1, pp. 975-977 (1995).*
Banker et al. "Modern Pharmaceutics", 3rd Ed. p. 596 (1996).*
CA Registry No. 921155-08-8, entered into CA Registry File on Feb. 15, 2007, supplied by Aurora Fine Chemicals.*
Aurora Fine Chemicals Product Guide.1 page, retrieved from the Internet at http://www.aurorafinechemicals.com/abouthtml on Apr. 28, 2015.*
CA Registry No. 904511-32-6, entered into CA Registry File on Aug. 25, 2006, supplied by Interbioscreen Ltd.*
CA Registry No. 902029-85-0, entered into CA Registry File on Aug. 17, 2006, supplied by Interbioscreen Ltd.*
CA Registry No. 900291-00-1, entered into CA Registry File on Aug. 10, 2006, supplied by Interbioscreen Ltd.*
Interbioscreen Product Guide, 1 page, retrieved from the Internet at http://www.ibscreen.com/products.shtml on Apr. 25, 2015.*
Jaquet et al. Small-Molecule NOX Inhibitors: ROS-Generating NADPH Oxidases as Therapeutic Targets, Antioxid Redox Signal. 2009, 11(10):2535-52.

* cited by examiner

*Primary Examiner* — Emily Bernhardt
(74) *Attorney, Agent, or Firm* — Emory Patent Group

(57) ABSTRACT

The disclosure relates to piperazine derivatives, compositions, and methods related thereto. In certain embodiments, the disclosure relates to inhibitors of NADPH-oxidase.

4 Claims, No Drawings

PIPERAZINE DERIVATIVES, COMPOSITIONS, AND USES RELATED THERETO

CROSS REFERENCE TO RELATED APPLICATIONS

This application claims priority to U.S. Provisional Application No. 61/496,161 filed Jun. 13, 2011, hereby incorporated by reference in its entirety.

STATEMENT REGARDING FEDERALLY FUNDED RESEARCH

This invention was made with government support under Grants RO1 CA 084138 awarded by the NIH. The government has certain rights in the invention.

FIELD

The disclosure relates to piperazine derivatives, compositions, and methods related thereto. In certain embodiments, the disclosure relates to inhibitors of NADPH-oxidase.

BACKGROUND

The NADPH-oxidase (Nox) enzymes represent a family of membrane enzymes (Nox1, Nox2, Nox3, Nox4, Nox5, Duox1, and Duox2) that catalyze NADPH-dependent generation of superoxide and/or hydrogen peroxide. While these enzymes have normal biological functions in signal transduction and host defense, they have also been implicated in the pathogenesis of a variety of diseases. Nox inhibitors have therapeutic uses and uses in biological assays. See Jaquet et al., 2009. Antioxid Redox Signal. 11(10):2535-52.

The core catalytic domain of Nox enzymes share similar structure, and their known biochemical function is the generation of reactive oxygen species (ROS). The basic catalytic subunit of Nox contains a C-terminal dehydrogenase domain featuring a binding site for NADPH and bound flavin adenine nucleotide (FAD), as well as an N-terminal domain consisting of six trans-membrane helices that bind two heme groups. Upon activation, NADPH transfers its electron to the FAD, which in turn passes electrons sequentially to two hemes and ultimately to molecular oxygen on the opposite side of the membrane to produce superoxide ($O_2$—) and/or hydrogen peroxide ($H_2O_2$), depending upon the isoform. Although Nox-isoforms catalyze the reduction of the molecular oxygen, they differ in their tissue distribution, their subunit requirement, domain structure, and mechanism by which they are activated. Depending upon the clinical condition, either isoform selective, or Nox/Duox pan-specific inhibitors are contemplated to be useful for therapeutic applications. Potential Nox inhibitors have been investigated, such as diphenylene iodonium (DPI), apocynin, Nox2 B-loop peptide, VAS2870, and pyrazolopyridines. However, no isoform- or class-selective Nox inhibitors have been approved in humans for treatment of diseases by the FDA. There exists a need to identify inhibitors for Nox enzymes.

SUMMARY

It has been discovered that certain compounds inhibit Nox enzymes. In some embodiments, the disclosure relates to compounds and methods of treating or preventing a Nox related disease or condition comprising administering to a subject a pharmaceutical composition comprising a compounds disclosed herein, derivatives, or compounds disclosed herein substituted with one or more substitutes including optional salt and prodrug forms. In certain embodiments, the disclosure relates to the use of compounds disclosed herein for the treatment or prevention of alcohol induced liver failure, traumatic brain injury (TBI), ischemia-reperfusion and neuropathic pain. In certain embodiments, contemplated compounds include those comprising Formula I,

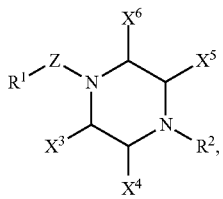

Formula I or pharmaceutically acceptable salt or prodrug thereof, wherein;

Z is S, SO, $SO_2$, C=O, C=S, C=N—$OR^8$;

$R^1$ and $R^2$ are each, the same or different, alkyl, carbocyclyl, aryl, or heterocyclyl, wherein $R^1$ and $R^2$ are optionally substituted with one or more, the same or different, $R^{10}$;

$R^8$ is hydrogen or alkyl optionally substituted with one or more, the same or different, $R^{10}$;

$X^3$, $X^4$, $X^5$, and $X^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^3$, $X^4$, $X^5$, and $X^6$ are each optionally substituted with one or more, the same or different, $X^{10}$; or $X^3$ and $R^1$ and the attached atoms form a polycyclic heterocyclyl optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$; and $X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is alkyl substituted with amino wherein the amino is substituted with an aryl group optionally substituted with one or more alkoxy or $R^1$ is a heterocyclyl optionally substituted with one or more $R^{10}$. Typically, the heterocyclyl is indolyl, quinolinyl, or imidazolyl.

In certain embodiments, the disclosure relates to compounds of Formula II as disclosed herein.

In certain embodiments, the disclosure relates to the use of a compound as described herein in the production of a medicament for the treatment of a Nox related disease. Compounds disclosed here can be contained in pharmaceutical compositions and administered alone or in combination with one or more additional active agents. The active agents can be administered simultaneously in the same dosage form or in separate dosage forms. Alternatively, the active agents can be administered sequentially in different dosage forms.

The compound can be combined with one or more pharmaceutically acceptable excipients to form a pharmaceutical composition. The compositions can be formulated for enteral, parenteral, topical, transdermal, or pulmonary administration. The compounds can be formulated for immediate release, controlled release, and combinations thereof. Examples of controlled release formulations include delayed release, extended release, pulsatile release, and combinations thereof.

The compounds described herein can be used to treat a variety of Nox-related diseases including, but not limited to, hypertension, chronic obstructive pulmonary disease (COPD), Alzheimer's disease (AD), Parkinson's disease (PD), acute respiratory distress syndrome (ARDS), acute lung injury (ALI), amyotrophic lateral sclerosis (ALS), atherosclerosis, aging-related deafness, inflammatory diseases, such as arthritis; various cancers such as colon cancer, prostate cancer, fibrotic diseases, such as liver fibrosis, pulmonary fibrosis, idiopathic pulmonary fibrosis, cirrhosis, endomyocardial fibrosis, mediastinal fibrosis, myelofibrosis, retroperitoneal fibrosis, nephrogenic systemic fibrosis, Crohn's disease, and scleroderma/systemic sclerosisreper, reperfusion injury-related disorders, such as myocardial infarction; ischemic stroke, preservation of organs during transplantation, ischemia/reperfusion injury (including stroke, myocardial infarction), diabetes, acute lung inflammation, cardiac hypertrophy, diabetic nephropathy, scar formation, skin aging and damage, and psoriasis.

In some embodiments, it is contemplated that compositions disclosed herein can be administered to subject before, during or after certain medical procedures, such as, organ transplants (heart, kidneys, liver, lungs, pancreas, intestine, and thymus) or other surgeries that reduce blood flow (cardiovascular surgery). The subject may be receiving or donating the organ.

In some embodiments, it is contemplated that composition disclosed herein can be used in biological (organ, tissue, or cell) storage mediums, typically aqueous solutions maintained at or below room temperatures, which may contain other ingredients such as, but not limited to, salts (sodium chloride, sodium lactate, calcium chloride, potassium chloride), amino acids, saccharides, polysaccharides (dextran, chondroitin, hydroxyethyl starch), vitamins (thiamine, ascorbic acid, calciferol, riboflavin, pyridoxine, tocopherol, cobalamins, phylloquinone, pantothenic acid, biotin, niacin, folic acid) and/or adenosine triphosphate or precursors (adenosine, inosine, and adenine).

In certain embodiments, the disclosure relates to method of making compounds disclosed herein by mixing starting materials and reagents disclosed herein under conditions such that the compounds are formed.

DETAILED DESCRIPTION

It has been discovered that piperazine analogs are Nox inhibitors. The disclosure relates to quinazoline derivatives, compositions, and methods related thereto. In certain embodiments, the disclosure relates to inhibitors of NADPH-oxidase, e.g., Nox1, Nox2, Nox3, Nox4, Nox5, Duox1 and/or Duox2.

Nox Inhibitors

In certain embodiments, the disclosure relates to compositions comprising a compound comprising Formula I,

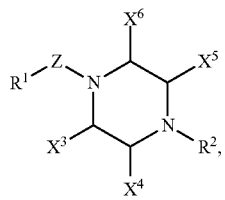

Formula I or pharmaceutically acceptable salt or prodrug thereof, wherein;

Z is S, SO, SO$_2$, C=O, C=S, C=N—OR$^8$;

$R^1$ and $R^2$ are each, the same or different, alkyl, carbocyclyl, aryl, or heterocyclyl, wherein $R^1$ and $R^2$ are optionally substituted with one or more, the same or different, $R^{10}$;

$R^8$ is hydrogen or alkyl optionally substituted with one or more, the same or different, $R^{10}$;

$X^3$, $X^4$, $X^5$, and $X^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^3$, $X^4$, $X^5$, and $X^6$ are each optionally substituted with one or more, the same or different, $X^{10}$; or $X^3$ and $R^1$ and the attached atoms form a polycyclic heterocyclyl optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^{10}$ is hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $X^{10}$ is optionally substituted with one or more, the same or different, $X^{11}$; and $X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is alkyl substituted with amino wherein the amino is substituted with an aryl group optionally substituted with one or more $R^{12}$ or $R^1$ is a heterocyclyl optionally substituted with one or more $R^{10}$. Typically, the heterocyclyl is indolyl, indolinyl, quinolinyl, or imidazolyl.

In certain embodiments, a composition comprising Formula I may have Formula IA,

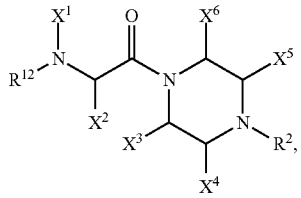

Formula IA or pharmaceutically acceptable salt or prodrug thereof, wherein;

$R^2$ is carbocyclyl, aryl, or heterocyclyl, wherein $R^2$ is optionally substituted with one or more, the same or different, $R^{10}$;

$X^1, X^2, X^3, X^4, X^5$, and $X^6$ are each, the same or different, hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $X^1, X^2, X^3, X^4, X^5$, and $X^6$ are each optionally substituted with one or more, the same or different, $X^{10}$;

$R^{10}$ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^{10}$ is hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein $X^{10}$ is optionally substituted with one or more, the same or different, $X^{11}$; and $X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^2$ is aryl, such as phenyl, optionally substituted with one or more, the same or different, $R^{10}$, and $R^{12}$ is aryl optionally substituted with one or more, the same or different, $R^{13}$.

In certain embodiments, all X are hydrogen or alkyl.

In certain embodiments, a composition comprising Formula I may have Formula IB,

Formula IB

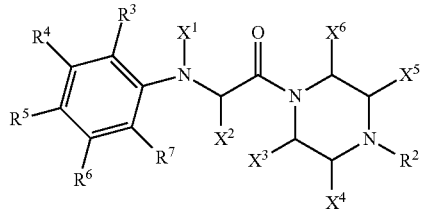

or pharmaceutically acceptable salt or prodrug thereof, wherein;

$R^2$ is carbocyclyl, aryl, or heterocyclyl, wherein $R^2$ is optionally substituted with one or more, the same or different, $R^{10}$;

$R^3$, $R^4$, $R^5$, $R^6$, and $R^7$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, and $R^7$ are each optionally substituted with one or more, the same or different, $R^{10}$;

$X^1$, $X^2$, $X^3$, $X^4$, $X^5$, and $X^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, $X^4$, $X^5$, and $X^6$ are each optionally substituted with one or more, the same or different, $X^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$; and $X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^5$ is halogen, alkyl, carboxy, alkoxycarbonyl, carbamoyl, alkylcarbamoyl, or alkanoyl, wherein $R^5$ is optionally substituted with one or more, the same or different, $R^{10}$.

In certain embodiments, $R^4$ is halogen.

In certain embodiments, $R^3$ is halogen.

In certain embodiments, all X are hydrogen or alkyl.

In certain embodiments, a composition comprising Formula I may have Formula IC,

Formula IC

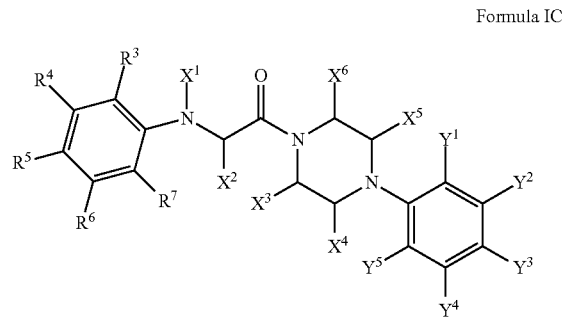

or pharmaceutically acceptable salt or prodrug thereof, wherein;

$Y^1$, $Y^2$, $Y^3$, $Y^4$, and $Y^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^1$, $Y^2$, $Y^3$, $Y^4$, and $Y^5$ are each optionally substituted with one or more, the same or different, $Y^{10}$;

$R^3$, $R^4$, $R^5$, $R^6$, and $R^7$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, and $R^7$ are each optionally substituted with one or more, the same or different, $R^{10}$;

$X^1$, $X^2$, $X^3$, $X^4$, $X^5$, and $X^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, $X^4$, $X^5$, and $X^6$ are each optionally substituted with one or more, the same or different, $X^{10}$; or $R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$; and $Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^5$ is halogen, alkyl, or alkanoyl, optionally substituted with one or more, the same or different, $R^{10}$.

In certain embodiments, $R^5$ is alkanoyl and $Y^3$ is hydroxy or alkoxy.

In certain embodiments, $R^4$ is halogen.

In certain embodiments, $R^3$ is halogen.

In certain embodiments, $Y^1$ is halogen, amino, hydroxy, or alkoxy.

In certain embodiments, $Y^2$ is halogen or alkoxy.

In certain embodiments, $Y^3$ is halogen, hydroxy, halogenated alkyl, amino, or alkoxy.

In certain embodiments, $Y^2$ and $Y^3$ is alkoxy.

In certain embodiments, all X are hydrogen or alkyl.

In certain embodiments, a composition comprising Formula I may have Formula ID,

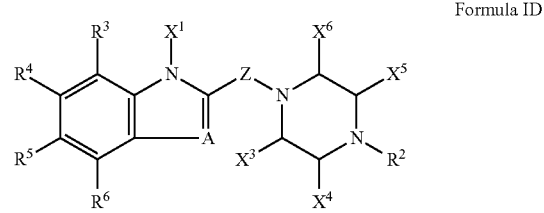

Formula ID or pharmaceutically acceptable salt or prodrug thereof, wherein;

----- is a single or double bond;

Z is S, SO, SO$_2$, C=O, C=S, C=N—OR$^8$;

A is N, CR$^9$, O, or S;

$R^2$ is carbocyclyl, aryl, or heterocyclyl, wherein $R^2$ is optionally substituted with one or more, the same or different, $R^{10}$;

$R^8$ is hydrogen or alkyl optionally substituted with one or more, the same or different, $R^{10}$;

$R^9$ is hydrogen, amino, or alkyl optionally substituted with one or more, the same or different, $R^{10}$;

$R^3$, $R^4$, $R^5$, and $R^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, and $R^6$ are each optionally substituted with one or more, the same or different, $R^{10}$;

$X^1$, $X^3$, $X^4$, $X^5$, and $X^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^3$, $X^4$, $X^5$, and $X^6$ are each optionally substituted with one or more, the same or different, $X^{10}$; or $R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$; and $X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^2$ is aryl optionally substituted with one or more, the same or different, $R^{10}$.

In certain embodiments, $R^5$ is hydrogen, halogen, hydroxy, nitro, alkyl, alkoxy, alkylsulfonyl, alkoxycarbonyl, alkylcarbamoyl, alkanoyl, carboxy, or carbamoyl optionally substituted with one or more, the same or different, $R^{10}$.

In certain embodiments, $R^4$ and $R^5$ is alkoxy;
In certain embodiments, $R^4$ is halogen.
In certain embodiments, $R^3$ is halogen.
In certain embodiments, A is N, CH, or CH$_2$.
In certain embodiments, all X are hydrogen or alkyl.
In certain embodiments, a composition comprising Formula I may have Formula IE,

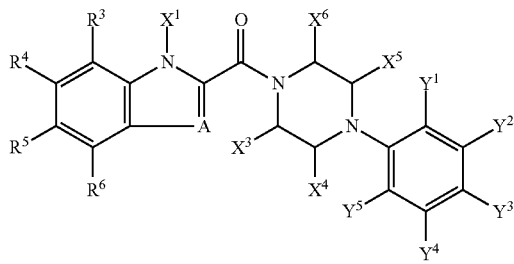

Formula IE or pharmaceutically acceptable salt or prodrug thereof, wherein;

A is N, or CR$^9$;

$R^9$ is hydrogen, amino, or alkyl optionally substituted with one or more, the same or different, $R^{10}$;

$Y^1$, $Y^2$, $Y^3$, $Y^4$ and $Y^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^1$, $Y^2$, $Y^3$, $Y^4$, and $Y^5$ are each optionally substituted with one or more, the same or different, $Y^{10}$;

$R^3$, $R^4$, $R^5$, and $R^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, and $R^6$ are each optionally substituted with one or more, the same or different, $R^{10}$;

$X^1$, $X^3$, $X^4$, $X^5$, and $X^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^3$, $X^4$, $X^5$, and $X^6$ are each optionally substituted with one or more, the same or different, $X^{10}$; or $R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$; and $Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, a composition comprising Formula I may have Formula IF,

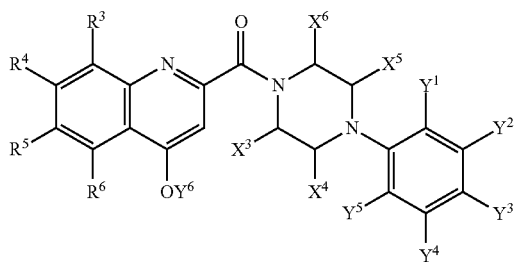

Formula IF or pharmaceutically acceptable salt or prodrug thereof, wherein;

$Y^1$, $Y^2$, $Y^3$, $Y^4$, $Y^5$ and $Y^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^1$, $Y^2$, $Y^3$, $Y^4$, $Y^5$ and $Y^6$ are each optionally substituted with one or more, the same or different, $Y^{10}$;

$R^3$, $R^4$, $R^5$, and $R^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, and $R^6$ are each optionally substituted with one or more, the same or different, $R^{10}$;

$X^3$, $X^4$, $X^5$, and $X^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^3$, $X^4$, $X^5$, and $X^6$ are each optionally substituted with one or more, the same or different, $X^{10}$; or $R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$; and $Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^4$ is halogen.

In certain embodiments, $R^5$ is alkanoyl.

In certain embodiments, all X are hydrogen or alkyl.

In certain embodiments, a composition comprising Formula I may have Formula IG,

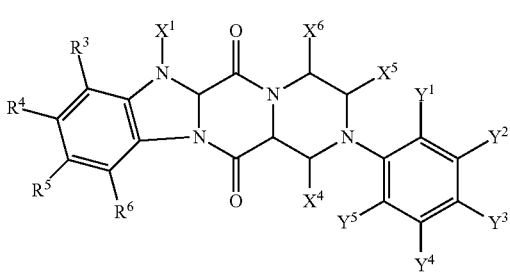

Formula IG or pharmaceutically acceptable salt or prodrug thereof, wherein;

$Y^1$, $Y^2$, $Y^3$, $Y^4$, and $Y^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^1$, $Y^2$, $Y^3$, $Y^4$, $Y^5$ and $Y^6$ are each optionally substituted with one or more, the same or different, $Y^{10}$;

$R^3$, $R^4$, $R^5$, and $R^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, and $R^6$ are each optionally substituted with one or more, the same or different, $R^{10}$;

$X^1$, $X^4$, $X^5$, and $X^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^4$, $X^5$, and $X^6$ are each optionally substituted with one or more, the same or different, $X^{10}$; or $R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$; and $Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, a composition comprising Formula I may have Formula IH,

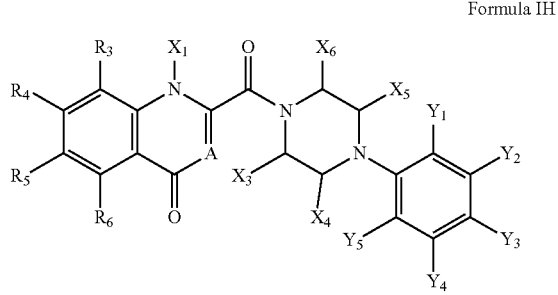

Formula IH or pharmaceutically acceptable salt or prodrug thereof, wherein;

A is N or $CX^2$;

$Y^1$, $Y^2$, $Y^3$, $Y^4$, and $Y^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^1$, $Y^2$, $Y^3$, $Y^4$, and $Y^5$ are each optionally substituted with one or more, the same or different, $Y^{10}$;

R³, R⁴, R⁵, and R⁶ are each, the same or different, hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R³, R⁴, R⁵, and R⁶ are each optionally substituted with one or more, the same or different, R¹⁰;

X¹, X², X³, X⁴, X⁵, and X⁶ are each, the same or different, hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein X¹, X², X³, X⁴, X⁵, and X⁶ are each optionally substituted with one or more, the same or different, X¹⁰; or R¹⁰ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹⁰ is optionally substituted with one or more, the same or different, R¹¹;

R¹¹ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹¹ is optionally substituted with one or more, the same or different, R¹²;

R¹² is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹² is optionally substituted with one or more, the same or different, R¹³;

R¹³ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

X¹⁰ is hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein X¹⁰ is optionally substituted with one or more, the same or different, X¹¹;

X¹¹ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

Y¹⁰ is hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein Y¹⁰ is optionally substituted with one or more, the same or different, Y¹¹; and Y¹¹ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, a composition comprising Formula I may have Formula IJ,

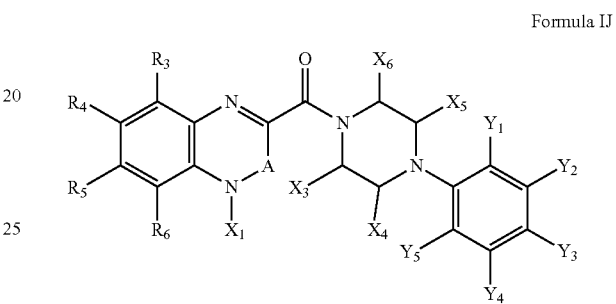

Formula IJ or pharmaceutically acceptable salt or prodrug thereof, wherein;

A is carbonyl;

Y¹, Y², Y³, Y⁴, and Y⁵ are each, the same or different, hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein Y¹, Y², Y³, Y⁴, and Y⁵ are each optionally substituted with one or more, the same or different Y¹⁰;

R³, R⁴, R⁵, and R⁶ are each, the same or different, hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R³, R⁴, R⁵, and R⁶ are each optionally substituted with one or more, the same or different, R¹⁰;

X¹, X³, X⁴, X⁵, and X⁶ are each, the same or different, hydrogen, alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein X¹, X³, X⁴, X⁵, and X⁶ are each optionally substituted with one or more, the same or different, X¹⁰; or R¹⁰ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹⁰ is optionally substituted with one or more, the same or different, R¹¹;

R¹¹ is alkyl, halogen, nitro, cyano, hydroxy, amino, mercapto, formyl, carboxy, carbamoyl, alkoxy, alkylthio, alkylamino, (alkyl)₂amino, alkylsulfinyl, alkylsulfonyl, arylsulfonyl, carbocyclyl, aryl, or heterocyclyl, wherein R¹¹ is optionally substituted with one or more, the same or different, R¹²;

R¹² is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$; and $Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compound of Formula I are selected from:
2-((4-acetylphenyl)amino)-1-(4-(4-methoxyphenyl)piperazin-1-yl)ethanone;
2-((4-acetylphenyl)amino)-1-(4-(4-methoxyphenyl)-3-methylpiperazin-1-yl)ethanone;
2-((4-isopropylphenyl)amino)-1-(4-(4-methoxyphenyl)piperazin-1-yl)ethanone;
2-((4-acetylphenyl)amino)-1-(4-(4-ethoxyphenyl)piperazin-1-yl)ethanone;
2-((3,4-difluorophenyl)amino)-1-(4-(4-methoxyphenyl)piperazin-1-yl)ethanone;
2-((3-fluorophenyl)amino)-1-(4-(4-methoxyphenyl)piperazin-1-yl)ethanone;
2-((4-acetylphenyl)amino)-1-(4-(3-methoxyphenyl)piperazin-1-yl)ethanone;
2-((4-acetylphenyl)amino)-1-(4-(2-methoxyphenyl)piperazin-1-yl)ethanone;
2-((4-acetylphenyl)amino)-1-(4-(4-fluorophenyl)piperazin-1-yl)ethanone;
2-((4-acetylphenyl)amino)-1-(4-(2-fluorophenyl)piperazin-1-yl)ethanone;
2-((4-acetylphenyl)amino)-1-(4-(pyridin-4-yl)piperazin-1-yl)ethanone;
2-((4-acetylphenyl)amino)-1-(4-(pyrimidin-2-yl)piperazin-1-yl)ethanone;
4-(4-(2-((4-acetylphenyl)amino)acetyl)piperazin-1-yl)benzonitrile;
2-((2-fluorophenyl)amino)-1-(4-(4-methoxyphenyl)piperazin-1-yl)ethanone;
2-((4-fluorophenyl)amino)-1-(4-(4-methoxyphenyl)piperazin-1-yl)ethanone;
2-((4-acetylphenyl)amino)-1-(4-(3,4-dimethoxyphenyl)piperazin-1-yl)ethanone;
2-((4-acetylphenyl)amino)-1-(4-(2-hydroxyphenyl)piperazin-1-yl)ethanone;
2-((4-acetylphenyl)amino)-1-(4-(3-hydroxyphenyl)piperazin-1-yl)ethanone;
2-((4-acetylphenyl)amino)-1-(4-(2-aminophenyl)piperazin-1-yl)ethanone; and
2-((4-acetylphenyl)amino)-1-(4-(4-hydroxyphenyl)piperazin-1-yl)ethanone or salts thereof.

In certain embodiments, compound of formula I are selected from:
1-(2-(4-(4-methoxyphenyl)piperazine-1-carbonyl)-1H-indol-5-yl)ethanone;
(5-methoxy-1H-indol-2-yl)(4-(4-methoxyphenyl)piperazin-1-yl)methanone;
(5-fluoro-1H-benzo[d]imidazol-2-yl)(4-(4-methoxyphenyl)piperazin-1-yl)methanone;
(5,6-dimethoxy-1H-indol-2-yl)(4-(4-methoxyphenyl)piperazin-1-yl)methanone;
(6-fluoro-1H-indol-2-yl)(4-(4-methoxyphenyl)piperazin-1-yl)methanone;
(5-fluoro-1H-indol-2-yl)(4-(4-methoxyphenyl)piperazin-1-yl)methanone;
1-(2-(4-(4-methoxyphenyl)piperazine-1-carbonyl)-3-methyl-1H-indol-5-yl)ethanone;
(5-hydroxy-1H-indol-2-yl)(4-(4-methoxyphenyl)piperazin-1-yl)methanone;
(5-fluoro-3-methyl-1H-indol-2-yl)(4-(4-methoxyphenyl)piperazin-1-yl)methanone;
(5-ethyl-1H-indol-2-yl)(4-(4-methoxyphenyl)piperazin-1-yl)methanone;
(5-bromo-1H-indol-2-yl)(4-(4-methoxyphenyl)piperazin-1-yl)methanone;
N-(5-methoxy-2-(4-(4-methoxyphenyl)piperazine-1-carbonyl)-1H-indol-3-yl)acetamide;
(4-(4-methoxyphenyl)piperazin-1-yl)(5-nitro-1H-indol-2-yl)methanone;
indolin-2-yl(4-(4-methoxyphenyl)piperazin-1-yl)methanone;
(1H-indol-2-yl)(4-(4-methoxyphenyl)piperazin-1-yl)methanone;
(4-(4-methoxyphenyl)piperazin-1-yl)(5-(methylsulfonyl)-1H-indol-2-yl)methanone;
methyl 2-(4-(4-methoxyphenyl)piperazine-1-carbonyl)-1H-indole-5-carboxylate;
2-(4-(4-methoxyphenyl)piperazine-1-carbonyl)-N-methyl-1H-indole-5-carboxamide;

2-(4-(4-methoxyphenyl)piperazine-1-carbonyl)-1H-indole-5-carboxamide;
(5-methoxy-1H-benzo[d]imidazol-2-yl)(4-(4-methoxyphenyl)piperazin-1-yl)methanone;
methyl 1-(5-fluoro-1H-benzo[d]imidazole-2-carbonyl)-4-(4-methoxyphenyl)piperazine-2-carboxylate;
2-(4-(4-methoxyphenyl)piperazine-1-carbonyl)-1H-indole-5-carboxylic acid;
1-(2-(4-(4-ethoxyphenyl)piperazine-1-carbonyl)-1H-indol-5-yl)ethanone;
(4-(4-ethoxyphenyl)piperazin-1-yl)(5-fluoro-1H-benzo[d]imidazol-2-yl)methanone;
1-(2-(4-(3-fluoro-4-methoxyphenyl)piperazine-1-carbonyl)-1H-indol-5-yl)ethanone;
1-(2-(4-(4-isopropoxyphenyl)piperazine-1-carbonyl)-1H-indol-5-yl)ethanone; and
(5-fluoro-1H-benzo[d]imidazol-2-yl)(4-(4-isopropoxyphenyl)piperazin-1-yl)methanone or salt thereof.

In certain embodiments, compound of Formula I are selected from:
(6-fluoro-4-hydroxyquinolin-3-yl)(4-(4-methoxyphenyl)piperazin-1-yl)methanone;
1-(4-hydroxy-3-(4-(4-methoxyphenyl)piperazine-1-carbonyl)quinolin-7-yl)ethanone; and
(8-fluoro-4-hydroxyquinolin-3-yl)(4-(4-methoxyphenyl)piperazin-1-yl)methanone or salts thereof.

In certain embodiments, the disclosure relates to compositions comprising Formula II,

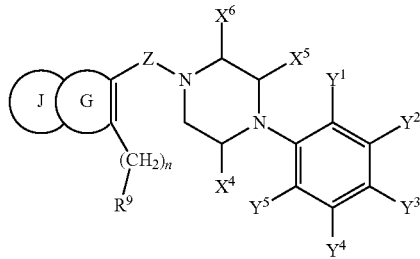

Formula II or pharmaceutically acceptable salt or prodrug thereof, wherein;

Z is S, SO, SO$_2$, C=O, C=S, C=N—OR$^8$, C=NHR$^8$, —(CH$_2$)$_m$—;

n is 1 to 10;

m is 1 to 10;

J and G are a bicyclic carbocyclyl, aryl, or heterocyclyl optionally substituted with one or more, the same or different, R$^5$;

R$^5$ is the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^5$ is optionally substituted with one or more, the same or different, R$^{10}$;

R$^8$ is hydrogen, cyano, or alkyl optionally substituted with one or more, the same or different, R$^{10}$;

R$^9$ is alkyl, amino, alkylamino, dialkylamino, carbocyclyl, aryl, or heterocyclyl, wherein R$^9$ is optionally substituted with one or more, the same or different, R$^{10}$;

X$^4$, X$^5$, and X$^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein X$^4$, X$^5$, and X$^6$ are each optionally substituted with one or more, the same or different, X$^{10}$;

Y$^1$, Y$^2$, Y$^3$, Y$^4$, and Y$^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein Y$^1$, Y$^2$, Y$^3$, Y$^4$, and Y$^5$ are each optionally substituted with one or more, the same or different, Y$^{10}$;

R$^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{10}$ is optionally substituted with one or more, the same or different, R$^{11}$;

R$^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{11}$ is optionally substituted with one or more, the same or different, R$^{12}$;

R$^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{12}$ is optionally substituted with one or more, the same or different, R$^{13}$;

R$^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

X$^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein X$^{10}$ is optionally substituted with one or more, the same or different, X$^{11}$;

X$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

Y$^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein Y$^{10}$ is optionally substituted with one or more, the same or different, Y$^{11}$; and Y$^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^9$ is amino, alkylamino, dialkylamino, piperidinyl, piperazinyl, or morpholinyl.

In certain embodiments, $R^5$ is halogen, alkyl, hydroxy, or alkoxy.

In certain embodiments, n is 1 or 2.

In certain embodiments, a composition comprising Formula II has Formula IIA,

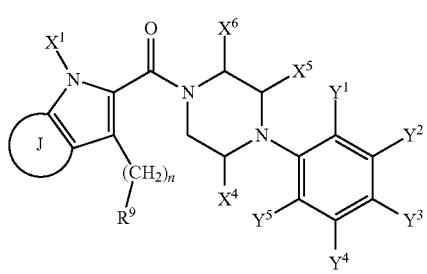

Formula IIA or pharmaceutically acceptable salt or prodrug thereof, wherein;

n is 1 to 10;

J is a carbocyclyl, aryl, or heterocyclyl optionally substituted with one or more, the same or different, $R^5$;

$R^5$ is the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^{10}$;

$R^9$ is alkyl, amino, alkylamino, dialkylamino, carbocyclyl, aryl, or heterocyclyl, wherein $R^9$ is optionally substituted with one or more, the same or different, $R^{10}$;

$X^1$, $X^4$, $X^5$, and $X^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^4$, $X^5$, and $X^6$ are each optionally substituted with one or more, the same or different, $X^{10}$;

$Y^1$, $Y^2$, $Y^3$, $Y^4$, and $Y^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^1$, $Y^2$, $Y^3$, $Y^4$, and $Y^5$ are each optionally substituted with one or more, the same or different, $Y^{10}$;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$; and $Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^5$ is halogen.

In certain embodiments, a composition comprising Formula II has Formula IIB,

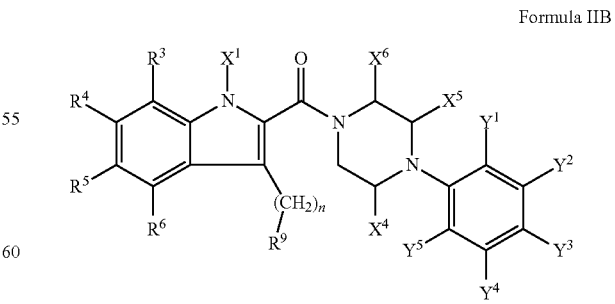

Formula IIB or pharmaceutically acceptable salt or prodrug thereof, wherein;

$R^9$ is alkyl, amino, alkylamino, dialkylamino, carbocyclyl, aryl, or heterocyclyl, wherein $R^9$ is optionally substituted with one or more, the same or different, $R^{10}$;

$Y^1$, $Y^2$, $Y^3$, $Y^4$, and $Y^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^1$, $Y^2$, $Y^3$, $Y^4$, and $Y^5$ are each optionally substituted with one or more, the same or different, $Y^{10}$;

$R^3$, $R^4$, $R^5$, and $R^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, and $R^6$ are each optionally substituted with one or more, the same or different, $R^{10}$;

$X^1$, $X^4$, $X^5$, and $X^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^4$, $X^5$, and $X^6$ are each optionally substituted with one or more, the same or different, $X^{10}$; or $R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$;

$R^{12}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{12}$ is optionally substituted with one or more, the same or different, $R^{13}$;

$R^{13}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$X^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$Y^{10}$ is hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $Y^{10}$ is optionally substituted with one or more, the same or different, $Y^{11}$; and $Y^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds of Formula II are selected from:

(3-(((2-(diethylamino)ethyl)amino)methyl)-5-fluoro-1H-indol-2-yl)(4-(4-methoxyphenyl)piperazin-1-yl)methanone;

(5-fluoro-3-(morpholinomethyl)-1H-indol-2-yl)(4-(4-methoxyphenyl)piperazin-1-yl)methanone;

(5-fluoro-3-(((1-methylpiperidin-4-yl)amino)methyl)-1H-indol-2-yl)(4-(4-methoxyphenyl)piperazin-1-yl)methanone;

(3-((4-ethylpiperazin-1-yl)methyl)-5-fluoro-1H-indol-2-yl)(4-(4-methoxyphenyl)piperazin-1-yl)methanone; and (3-((diethylamino)methyl)-5-fluoro-1H-indol-2-yl)(4-(4-methoxyphenyl)piperazin-1-yl)methanone or salts thereof.

Nox Related Diseases

Studies from the knockout mice suggest that Nox2 is an important biological target for modulation of alcohol induced liver failure, traumatic brain injury (TBI), ischemia-reperfusion and neuropathic pain. In addition, the major source of harmful ROS in transplanted organs appears to be Nox enzymes, so Nox inhibitors are expected to be useful to preserve organ function during transplantation of hearts, kidneys, etc.

NADPH oxidases (Nox) and Dual Oxidases (Duox) are family of 7 membrane enzymes (Nox1, Nox2, Nox3, Nox4, Nox5, Duox1 and Duox2) whose sole function is to generate superoxide and hydrogen peroxide. While these enzymes have normal biological functions in signal transduction, host defense against microbes, and response to environmental stresses, recent studies suggest that the enzymes play a central role in cell and tissue pathology that occurs in diseases such as those mentioned above. Therefore, small molecule inhibitors are predicted to be of therapeutic value in the treatment of these conditions. Proof of concept has been obtained for many of these diseases using Nox-isoform-deleted mouse disease models. For example, Nox2 knockout mice show a 55% improvement in lesion size in models of traumatic brain injury.

The core catalytic domain of all 7 Nox enzymes share similar structure. The basic catalytic subunit of Nox contains a C-terminal dehydrogenase domain featuring a binding site for its substrate NADPH and bound flavin adenine nucleotide (FAD), as well as an N-terminal domain consisting of six trans-membrane alpha-helices that bind two heme groups. Upon activation, NADPH transfers its electron to the FAD, which in turn passes electrons sequentially to the two heme groups and ultimately to molecular oxygen on the opposite side of the membrane to produce superoxide ($O_2^-$) and/or hydrogen peroxide ($H_2O_2$), depending upon the isoform. Although all seven Nox-isoforms catalyze the reduction of the molecular oxygen, they differ in their tissue distribution, their subunit requirement, domain structure, and mechanism by which they are activated. Depending upon the clinical condition, either isoform-selective, or Nox/Duox pan-specific inhibitors are predicted to be useful for drug development.

Reactive oxygen species (ROS) cause molecular damage to DNA, proteins, and lipids, and can perturb normal signal transduction pathways. Elevated ROS levels are seen in a variety of diseases, and are recognized as a major contributor to cell and tissue injury in these conditions. These diseases include, but are not limited to, hypertension, ischemia/reperfusion injury (including stroke, myocardial infarction, transplanted organs), diabetes, atherosclerosis, Alzheimer's disease, chronic obstructive pulmonary disease, various cancers, acute respiratory distress syndrome (ARDS), acute lung inflammation, Parkinson's disease, pulmonary fibrosis, liver fibrosis, cardiac hypertrophy, diabetic nephropathy, diabetic neuropathy, scar formation, skin aging and damage, psoriasis and others.

Thus, within certain embodiments, this disclosure contemplates use of compounds and compositions disclosed for the treatment or prevention of Nox related diseases.

Nox-generated ROS can participate in immune function in a variety of ways, which are not mutually exclusive. First, the reactive oxygen itself or its by-products such as HOCl and peroxinitrite can directly oxidize biomolecules in invading microbes in a fairly nonspecific manner, resulting ultimately in molecular damage and microbial cell death. High abundance Nox enzymes and those that are coexpressed with cooperating enzymes such as peroxidases and nitric oxide (NO) synthase are the most likely candidates for this sort of mechanism. Second, the reactive oxygen can participate in signal transduction mechanisms linked to immunity and inflammation. This occurs through the selective oxidation of specific signaling enzymes/proteins that are linked to processes such as the secretion of cytokines or the activation of other killing mechanisms. Such signaling targets include transcription factors such as NF-κB, signaling proteins such as protein kinases and phosphatases, and ion and/or proton channels.

Nox-derived ROS mediated by professional phagocytes such as neutrophils and macrophages important in innate immunity. These cells express very large amounts of gp91phox, now also called Nox2, along with its regulatory subunits p47phox, p67phox, p40phox, and Rac2. In addition, myeloperoxidase (MPO) is secreted into the phagosome where it converts $H_2O_2$ (produced by Nox2) plus chloride into HOCl; the latter has a direct microbicidal effect.

In addition, macrophages produce large amounts of NO during phagocytosis; when NO reacts with superoxide, it generates the highly cytotoxic chemical species peroxinitrite (HONO). The activity of the phagocyte NADPH oxidase also triggers opening of proton and possibly potassium channels, that are proposed to change the ionic environment of the phagosome, thereby activating microbicidal proteases and contributing to microbial killing.

Neutrophil-derived ROS, including superoxide and $H_2O_2$ generated by Nox2, HONO generated from superoxide and nitric oxide, and HOCl generated by MPO, have been implicated in the tissue damage seen in acute and chronic inflammatory conditions in which there is at some stage in the disease a neutrophil or macrophage infiltrate. Such conditions include acute and chronic infections, autoimmune conditions such as inflammatory bowel disease, adult respiratory distress syndrome (also called "shock lung"), arthritis, and any number of other inflammatory conditions.

Thus, within certain embodiments, this disclosure contemplates use of compounds and compositions disclosed for the treatment or prevention of inflammatory bowel disease, adult respiratory distress syndrome, arthritis, and any number of other inflammatory conditions.

Lactoperoxidase (LPO) catalyzes the $H_2O_2^-$ dependent oxidation of the anion thiocyanate to form the antimicrobial compound HOSCN that prevents growth of bacteria, fungi, and viruses. Epithelial cells in salivary ducts express Duox2, and those in trachea and bronchus express Duox1; these Duox enzymes are likely to play a role in humans as a source of $H_2O_2$ for LPO-dependent antimicrobial activity. Induction of Nox1 and other mucosal Nox enzymes by cytokines and bacterial products provides evidence for a role for Nox/Duox enzymes in mucosal innate immunity, although it should also be noted that Nox1 is induced by a variety of other agonists including growth factors, consistent with other roles such as mitogenic regulation.

Hypoxia sensing and related signaling events including activation of hypoxia-inducible factor 1 (HIF-1) represent important features of lung cell physiology and lung function. Up-regulation of Nox1 mRNA and protein occurred during hypoxia, accompanied by enhanced reactive oxygen species (ROS) generation; the latter was accompanied by activation of HIF-1-dependent gene expression, which was blocked by catalase. Thus, hypoxic upregulation of Nox1 and subsequently augmented ROS generation may activate HIF-1-dependent pathways and participate in adaptation to high altitude.

Increasing evidence points to a role for Nox-dependent ROS in both fibrotic diseases and the alveolar cell death that leads to emphysema. Airway epithelial cells are both exposed to and produce cytokines and ROS in inflammatory settings and on exposure to cigarette smoke. Some lung fibrotic diseases are associated with increased TGF-β1 in the airway. This cytokine induces $H_2O_2$ production in lung fibroblasts, which in the presence of heme-type peroxidases such as LPO and MPO, can mediate oxidative cross-linking of tyrosine residues in extracellular matrix proteins, resulting in lung fibrosis. Fibroblasts isolated from the lungs of patients with idiopathic pulmonary fibrosis generated $H_2O_2$ in response to TGF-β1, and induced death in cocultured small airway epithelial cells. ROS produced in lung epithelial cells activated JNK and caused cell death via TNF-RI and the TRAF2-ASK1 signaling axis. Cigarette smoke may also contribute to obstructive pulmonary disease via Nox-generated ROS. Cigarette smoke and the bacterial product LPS both up-regulate NOXO1 the activator of Nox1. TLR4 deficiency, which causes emphysema in mice, up-regulated Nox3 in lung and endothelial cells resulting in increased oxidant generation and elastolytic activity. Treatment of Tlr4(−/−) mice or endothelial cells with chemical Nox inhibitors or Nox3 siRNA prevented the disease development.

Thus, within certain embodiments, this disclosure contemplates use of compounds and compositions disclosed for the treatment or prevention of lung diseases such as, but not limited to, fibrosis, obstructive pulmonary disease, emphysema, and asthma.

Oxidant/antioxidant imbalance is recognized as an important contributor to asthma. In addition to the Nox2 system, which is highly expressed in inflammatory cells including the eosinophils that are recruited to the asthmatic lung, airway smooth muscle cells express Nox enzymes, particularly Nox4, which have been proposed to contribute to tissue destruction in asthma. In addition, pollen itself contains an endogenous NADPH oxidase activity, which functions to generate local signals in airway epithelium. These signals in turn trigger the early recruitment of granulocytes, contributing to allergic inflammation in the lung and eye.

Thus, within certain embodiments, this disclosure contemplates use of compounds and compositions disclosed for the treatment or prevention of allergic inflammation.

Human urotensin II, which is implicated in pulmonary hypertension, potently induced p22phox and Nox4 in lung smooth muscle, markedly increasing ROS levels that activate ERK1,2, p38 MAPK, Jun Kinase, and Akt. This perturbed redox-dependent signaling is proposed to contribute to smooth muscle hypertrophy and proliferation that is associated with pulmonary hypertension.

Thus, within certain embodiments, this disclosure contemplates use of compounds and compositions disclosed for the treatment or prevention of pulmonary hypertension.

Nox enzymes are expressed in vascular smooth muscle, adventitia, and endothelium, and are the major physiologic source of ROS in these tissues in the absence of infiltration by inflammatory cells. Nox2 and Nox4 are both expressed in endothelium and where under some conditions they participate in cell proliferation while Nox1, Nox4, and Nox2 are expressed in vascular smooth muscle cells. Nox1 in vascular smooth muscle participates in cell proliferation, while Nox4 in these cells participates in maintenance of the differentiated phenotype. Nox2 and associated regulatory proteins are also expressed in adventitia, where they contribute to constitutive ROS generation and to Angiotensin II-induced vascular tone in part through inactivation of NO by superoxide.

Both Nox2 and Nox4 are expressed in cardiomyocytes. Nox4 is necessary for the differentiation of mouse embryonic stem cells or fibroblasts into myocytes. In addition, Nox4 may contribute to the pathological activation of cardiac fibroblasts in cardiac fibrosis associated with heart failure. Increased ROS is also associated with left ventricular hypertrophy (LVH), and this correlates with overexpression of Nox2 in Angiotensin II-induced LVH, and, in pressure overload LVH, with both Nox4 and Nox2. Aldosterone/Angiotensin II-mediated interstitial cardiac fibrosis is mediated by Nox2-dependent ROS generation. Nox enzymes are likely to contribute to the occurrence of and tissue damage seen in myocardial infarction by several mechanisms. Nox2 overexpression in cardiomyocytes is seen following myocardial infarction, and may result in a sustained increase in ROS. Ischemia followed by reperfusion is implicated in increased myocardial injury following infarction, and is mediated by increased ROS; reperfusion injury is associated with increased circulating and myocardial levels of cytokines, which are associated with increased levels of Nox1, Nox2, and Nox4. Myocardial Nox2 also contributes to superoxide production in the fibrillating human atrial myocardium where it may play an important role in the cardiac oxidative injury and electrophysiological remodeling seen in patients with atrial fibrillation.

Thus, within certain embodiments, this disclosure contemplates use of compounds and compositions disclosed for the treatment or prevention of ischemia and heart failure.

In normal physiology, Nox enzymes participate in vascular smooth muscle signaling: Nox-derived ROS in vascular smooth muscle cells regulate the activity of the signaling proteins p38 MAPK and Akt, and are essential for Angiotensin II-induced calcium fluxes. Nox-derived ROS can also affect the local bioavailability of the vaso-protective signal molecule NO.

Nox2 has been implicated in some models of hypertension. Nox2 accounts for significant ROS generation in vascular smooth muscle in resistance arteries and in endothelium. In a model of renovascular hypertension Nox2-derived superoxide decreased NO bioavailability, and there was marked protection from hypertension in the Nox2 (−/−) mice. In low renin salt-sensitive hypertension, a tat-peptide inhibitor of Nox2 normalized ROS generation and endothelium-dependent vascular relaxation. Thus, increasingly, evidence points to the role of Nox enzymes in the vascular remodeling associated with hypertension.

Thus, within certain embodiments, this disclosure contemplates use of compounds and compositions disclosed for the treatment or prevention of hypertension.

Human atherosclerotic plaques express large amounts of Nox2, which was localized to the plaque shoulder, an area that is rich in macrophages. Approximately 60% of the ROS in atherosclerotic plaques arises from Nox enzymes, particularly Nox2. Oscillatory sheer stress occurs preferentially in branched or curved regions of arteries and is associated with atherogenesis. Oscillatory sheer stress results in several-fold induction of Nox1, Nox2, and Nox4 in vascular endothelium (with opposite effects of the antiatherogenic laminar flow that occurs in straight portions of vessels). Oscillatory sheer stress is associated with induction of bone morphogenic protein 4 (BMP4), which induces Nox1 and p47phox, resulting in an oxidative stress that leads to ICAM-1 expression and monocyte adhesion. Nox1 expression increases 3-fold following balloon injury and precedes restenosis and atherosclerosis. This in turn led to monocyte infiltration and a vicious cycle of increasing oxidant stress. Peripheral artery disease, like coronary artery disease, is also associated with evidence of oxidative stress and treatment with an antioxidant improved arterial flow parameters.

The mechanisms by which Nox-derived oxidative stress induces atherogenesis and arterial disease may include direct molecular damage by ROS [including "uncoupling" of nitric oxide synthase that results in a further increase in ROS], increased expression of proatherosclerotic genes, induced differentiation of adventitial fibroblasts into myofibroblasts (a feature of the vascular remodeling seen in atherosclerosis), and induction of VEGF which contributes to the growth of new microvessels into atheromatous plaques. Chronic activity of Nox enzymes inactivate telomerase and may promote senescence of endothelial progenitor cells. Therefore, inhibition of Nox2 and/or Nox1 is likely to be useful for the prevention and treatment of arterial disease and arthrerosclerosis. Thus, within certain embodiments, this disclosure contemplates use of compounds and compositions disclosed for the treatment or prevention of atherosclerosis and peripheral artery disease.

Chronic hyperglycemia is directly linked to microvascular complications that cause blindness, atherosclerosis, and neuropathy. This link involves biochemical abnormalities including increased polyol pathway flux, increased formation of advanced glycation end products (AGEs), activation of protein kinase C, and increased flux through the hexosamine pathway. These pathways seem to result from overproduction of ROS, and antioxidants are protective against deleterious effects of high glucose on vascular endothelial cells. Nox enzymes, particularly the Rac-regulated enzymes Nox1 and Nox2, play a role in endothelial dysfunction in the setting of diabetes mellitus. Consistent with a role for these Nox isoforms, dominant negative Rac1 protected against oxidative stress and endothelial dysfunction in a mouse model of diabetes. Indeed, impaired activation of Rac1 and Nox-dependent oxidative stress has been proposed to underlie some of the vascular protective effects of statins. Some of the cardiovascular pathologies seen in diabetes may be mediated by the glycated proteins that result from high glucose. For example, glycated BSA stimulated Nox2-dependent ROS production via a protein kinase C-dependent mechanism, resulting in NF-κB activation and induction of inflammatory genes.

Thus, within certain embodiments, this disclosure contemplates use of compounds and compositions disclosed for the treatment or prevention of blindness and neuropathy in a diabetic subject.

Nox4 is expressed in high levels in kidney, while other Nox1, Nox2, and Nox regulatory subunits are expressed at lower but quantitatively significant levels, making Nox enzymes attractive candidates for the origin of renal ROS including the relatively high levels of $H_2O_2$ seen in urine. In kidney, Nox-dependent ROS is produced in response to agonists that bind to D1-like receptors, to Angiotensin II and to $H^+$ fluxes. Nox enzymes have been suggested to function in normal renal physiology in secretion of erythropoietin, in renal regulation of blood pressure, in regulation of mesangial cell protein synthesis, and in innate immunity.

Thus, within certain embodiments, this disclosure contemplates use of compounds and compositions disclosed for the treatment or prevention of kidney-related diseases.

While elevated glucose in diabetes affects a variety of tissues, kidney is particularly susceptible, responding with renal hypertrophy, fibrosis, glomerular enlargement, and hyperfiltration of protein. In proximal tubules, high glucose stimulates ROS production, resulting in increased expression of angiotensinogen with consequent systemic effects, e.g., on blood pressure. Apocyanin, an inhibitor of Nox2 and probably other Nox enzymes, was used in rats to test the hypothesis that ROS from a Nox underlies the development of diabetic nephropathy. Diabetes mellitus increased excretion of $H_2O_2$, lipid peroxidation, and protein. Kidneys of rats with diabetes mellitus had increased expression of Nox2, p47phox, and Nox4, increased membrane translocation of p47phox (reflecting Nox2 activation), and increased mesangial matrix. Apocyanin prevented the increased $H_2O_2$, lipid peroxidation, and protein in diabetic rats, prevented the increased renal expression of Nox2 and membrane translocation of p47phox, and blocked the mesangial matrix expansion. Biochemical effects of elevated ROS included inhibition of $Na^+$/glucose cotransport, increased secretion of TGF-beta1, and activation of NF-κB signaling. PKC-beta(−/−) diabetic mice were protected against induction of Nox2, Nox4, and glucose-induced renal dysfunction and fibrosis, indicating a role for PKC in Nox expression and renal pathology. Nox4 is a major source of ROS in diabetic nephropathy, based on protection against high glucose-induced ROS generation and fibronectin expression in kidney cells transfected with Nox4 antisense oligonucleotides.

Thus, within certain embodiments, this disclosure contemplates use of compounds and compositions disclosed for the treatment or prevention of diabetic nephropathy.

ROS play an important role in the pathogenesis of glomerulopathies and renal failure, and antioxidants are useful in preventing or treating disease. Active Heymann nephritis (AHN) is a model of human membranous nephropathy, and is associated with oxidant—antioxidant imbalance, which contributes to renal damage. Likewise, glomerular mesangial injury in rats treated chronically with aldosterone and salt is associated with induction of Nox2, Nox4, and p22phox, increased p47phox and p67phox in the membrane fraction (indicating activation of the Nox2 system), and increased renal ROS. In an Angiotensin II-induced mesangioproliferative model of glomerulonephritis, Nox2 and Nox4 induction were associated with disease progression, and treatment with the antioxidant probucol in combination with Angiotensin II receptor blockade fully arrested disease progression and proteinuria.

Thus, within certain embodiments, this disclosure contemplates use of compounds and compositions disclosed for the treatment or prevention of nondiabetic renal failure and glomerulonephropathies. The composition may be administered in combination with Angiotensin II receptor blockers, such as losartan, irbesartan, olmesartan, candesartan, valsartan, and telmisartan.

Acute tubular necrosis secondary to ischemic renal failure is a common and serious clinical problem. Reactive oxygen and phagocyte-mediated inflammation play central roles in this process, and antioxidant therapy is beneficial. Thus, within certain embodiments, this disclosure contemplates use of compounds and compositions disclosed for the treatment or prevention of acute tubular necrosis.

In general, renal oxidative stress can precede and contribute to hypertension from several origins, and if corrected, can lower blood pressure. Angiotensin II-infused rodents show increased renal and systemic expression of Nox1, which contributes to the development and maintenance of hypertension. Nox enzymes may also contribute to a genetic predisposition to renal hypertension. Genetically salt-sensitive rats show a 3-fold higher expression of renal Nox1 compared with control rats, and overexpression was associated with increased activity of ERK1,2 and JNK kinases. Mechanistically, the regulation of tubular transport by ROS is important to overall salt and water balance and therefore to blood pressure: superoxide stimulates NaCl absorption by the thick ascending limb by activating protein kinase C and by blunting the effects of NO. Hyperleptinemia also induces hypertension, which may be mediated by its stimulation of both systemic and renal oxidative stress, which decreases the amount of bioactive NO and causes renal sodium retention by stimulating tubular sodium resorption.

Inflammation and consequent oxidative stress are induced by hemodialysis and is linked to the acceleration of tissue damage in end-stage renal disease. Interleukins and anaphylatoxins produced during hemodialysis are potent activators of Nox enzymes, providing a possible link between Nox activation and tissue damage. The resulting oxidative stress is implicated in long-term complications including anemia, amyloidosis, accelerated atherosclerosis, and malnutrition.

Cancer and rapidly proliferating cells were frequently noted to overproduce reactive oxygen, and antioxidants and inhibitors of NADPH oxidases were associated with decreased cell proliferation. In many of cases, the source of this ROS is Nox enzymes: this includes melanoma (Nox4) prostate cancer (Nox5 and Nox1) glioblastoma (Nox4 and sometimes Nox5), *H. pylorus*-induced gastric inflammation leading to gastric cancer (Nox1), and Barrett's esophageal adenocarcinoma (Nox5). Reports, have observed an increase in Nox1 expression in colon cancer. Nox1 protein and mRNA are overexpressed beginning at the adenoma (precancerous stage), and did not further increase at later stages. Overexpression showed a strong correlation with oncogenic mutations in K-Ras, and markedly elevated Nox1 levels in the intestinal tract were also seen in mice that expressed V12 K-Ras in intestinal epithelium.

A causal role for Nox overexpression or activation in cancer is supported by several lines of evidence. Nonphagocyte Nox enzymes were implicated in cell division and suggested to play a role in cell transformation and cancer. Decreasing the expression of Nox1 (originally called Mox1) decreased cell division in vascular smooth muscle and in V12-K-Ras transformed NRK cells. Suppression of Nox5 expression in Barrett's esophageal adenocarcinoma cells likewise inhibited proliferation. Nox-dependent effects on cell division, angiogenesis, cell survival, and integrin signaling provide plausible mechanisms by which Nox enzymes may be linked to cancer development. Thus, within certain embodiments, this disclosure contemplates use of compounds and compositions disclosed for the treatment or prevention of cancers disclosed herein.

Nox overexpression may influence cancer by increasing the rate of cell division. Proliferating keratinocytes showed higher ROS generation and Nox1 levels than quiescent cells. Overexpression of Nox1 in several cell types is associated with increased cell division. In fibroblasts that overexpressed heterologous Nox1 and also harbored an oncogenic mutation in Ras, overexpression of catalase markedly decreased mitogenic growth, the transformed phenotype and tumorigenicity in athymic mice, implicating Nox-derived $H_2O_2$ in the tumor phenotype. The mechanism of mitogenic stimulation involves several redox-sensitive steps. In actively cycling cells, Nox1 stimulated proliferation by reducing the requirement for growth factors to maintain expression of cyclin D1, whereas during cell cycle reentry, Nox1 activity was required for transcriptional activation of Fos family genes.

In studies in prostate tumor cells that overexpressed Nox1, Nox1-derived $H_2O_2$ had only a small effect on mitogenic rate in culture. However, in animals, Nox1 overexpression markedly increased angiogenesis by inducing the angiogenic factor VEGF correlating with an aggressive tumor phenotype. A similar role for Nox1 in angiogenesis in atherosclerosis has been proposed.

In contrast to the frequently reported proapoptotic effect of ROS, ROS from Nox4 in pancreatic cells and from Nox1 in colon adenoma and carcinoma inhibit apoptosis. In pancreatic cancer cells, depletion of Nox4 or ROS triggered apopotosis predicting a therapeutic effect of Nox inhibition in treating this type of cancer. Cell survival involved activation of NF κ-B- and Akt-dependent prosurvival pathways.

Cancer cell phenotype including mitogenic rate and response to chemotherapy is profoundly affected by attachment to extracellular matrix (ECM). Nox enzymes affect both ECM synthesis and structure, and mediate the cellular effects of ECM. In colon carcinoma cells, Nox1 controls the expression of specific integrins at the cell surface, and integrin-dependent attachment/signaling stimulates the G1/S transition. In A431 carcinoma cells, the growth factor EGF activates Nox-dependent ROS generation, and this in turn regulates expression of integrins, cell attachment properties, and cell survival. In pancreatic cancer cells, ECM stimulated ROS production through Nox4 resulting in increased cell survival. These studies emphasize the interplay between ROS and ECM in effecting the cancer phenotype.

ROS play a role both in normal neurological processes and in neurological disease states. NGF stimulates ROS generation in PC12 cells in a Rac1-dependent manner, and NGF-generated ROS participates in neuronal differentiation. ROS in neurons also enhances voltage-gated $K^+$ currents elicited by NGF, mediated by activation of NF-κB. H2O2 inhibits synaptic transmission in hippocampus and other areas of the brain by complex mechanisms that are not yet fully elucidated. In guinea pig striatal slices, $H_2O_2$ production was $Ca^{2+}$-dependent and modulated neurotransmitter release, revealing a signaling role for ROS in synaptic transmission. A possible target is the fusion protein SNAP25, which may function as a presynaptic ROS sensor.

Specific roles for Nox enzymes in nerve and brain are beginning to come to light. Nox2 is expressed in relatively high levels in microglia, the principal immune effector cell in the brain, where it participates in host defense and inflammatory responses in this organ. Nox4 is expressed in neurons and capillaries of the brain, and is up-regulated during ischemia. Neuronal Nox1 is induced in response to NGF, and suppresses neurite outgrowth. Nox5 shows significant expression in cerebrum and Duox1 is highly expressed in cerebellum. To date, there have been no detailed reports cataloging the expression of specific Nox enzymes in subregions of the brain. Remarkably, Nox1 knockout mice show a marked change in their ability to perceive inflammatory pain, i.e., decreased thermal hyperalgesia produced by inflammation, compared with wild-type mice (Ibi and Yabe-Nishimura, unpublished personal communication). Thus, within certain embodiments, this disclosure contemplates use of compounds and compositions disclosed for the treatment or prevention of inflammatory pain control.

Within certain embodiments, this disclosure contemplates use of compounds and compositions disclosed for the treatment or prevention of Alzheimer's disease Among the characteristic changes seen in Alzheimer's disease (AD) are extracellular deposits of fibrillar β-amyloid protein (plaques) and neuronal loss resulting in progressive cognitive impairment. While the underlying early cause(s) of AD remains elusive, evidence points to inflammatory reactions as a key component in the progressive neuronal loss. Microglia are thought to be a major cell type that mediates this inflammatory response, which involves secretion of inflammatory cytokines and release of ROS and reactive nitrogen species, although astrocytes may also play a role. Chronic production of inflammatory mediators results in neuronal death, either by direct oxidative damage or by overactivating death-promoting signaling systems including NF-κB.

Evidence for excessive oxidant production in AD comes from autopsy studies and animal models. Markers of oxidative stress in AD brains occurred early, and increased with severity of the disease. Oxidative damage could be detected prior to observation of plaques both in human and in animal models, pointing to inflammation as an early event in AD. The major source of oxidants is generally thought to be the microglial and/or astrocyte Nox2-type system and there is also increased expression of Nox1 and Nox3 in AD brain.

Within certain embodiments, this disclosure contemplates use of compounds and compositions disclosed for the treatment or prevention of Parkinson's disease Parkinson's disease (PD) is a complex disorder that results in the progressive degeneration of dopaminergic neurons in the substantia nigra. Although the origin is unclear, oxidative stress has been thought to play a role in its pathogenesis, and the condition can be recapitulated experimentally by administration of MPTP (1,2,3,6-tetrahydropyridine), which results in increased ROS by inhibiting mitochondrial respiration and by activating Nox2 in microglia. While defects in mitochondrial Complex I may underlie sporadic PD, activated or induced Nox enzymes in microglia may play a synergistic role. In model systems, LPS administration acutely activates the microglial inflammatory response, releasing proinflammatory factors, activating glial Nox2, and producing neuronal loss. In this model of Parkinson's disease, Nox2 knockout mice were significantly protected against loss of nigral dopaminergic neurons. In a more natural setting, substance P produced in substantia nigra can also activate glial Nox2, and could play a role in PD.

Within certain embodiments, this disclosure contemplates use of compounds and compositions disclosed for the treatment or prevention of amyotrophic lateral sclerosis (ALS) ALS is a progressive and ultimately fatal loss of spinal cord motor neurons. SOD1 is mutated in familial forms of the disease. However, markers of oxidative damage are seen in sporadic cases of ALS, and an inflammatory interplay between neuronal and glial cells mediated by cytokines has been observed. The Nox2 system was found to be activated in the spinal cord of patients with ALS and in genetic animal models of this disease. Importantly, inactivation of Nox in ALS mice delayed neurodegeneration and extended survival.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more Nox inhibitors can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the Nox inhibitor(s) to carrier and/or other substances may vary from about 0.5 to about 100 wt. % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid) (anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more Nox inhibitors. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., Nox inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The Nox inhibitors described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the Nox inhibitors can be administered in the same dosage form or in separate dosage forms with one or more other active agents.

Specific examples of compounds that can be adjunctively administered with the Nox inhibitors include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenyloin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

The additional active agent(s) can be formulated for immediate release, controlled release, or combinations thereof.

Terms

As used herein, "alkyl" means a noncyclic straight chain or branched, unsaturated or saturated hydrocarbon such as those containing from 1 to 10 carbon atoms, typically 1 to 6 carbon atoms. Within any embodiments herein, alkyl may refer to an alkyl with 1 to 6 carbons ($C_{1-6}$alkyl). Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butyryl, 2-butyryl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—$CH_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—$CH_3$).

"Alkanoyl" refers to an alkyl as defined above attached through a carbonyl bride
(i.e., —(C=O)alkyl).

"Alkyloxycarbonyl" refers to an alkyl as defined above attached through a carboxy bridge (i.e., —(C=O)Oalkyl.

"Alkylcarbamoyl" refers to an alkyl as defined above attached through a carbonyl bridge (i.e., —(C=O)NHalkyl).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfonamide" refers to an alkyl as defined above attached through a sulfamoyl bridge (i.e., —S(=O)$_2$NHalkyl), and an "Arylsulfonamide" refers to an alkyl attached through a sulfamoyl bridge (i.e., (i.e., —S(=O)$_2$NHaryl).

"Alkylsulfinyl" refers to an alkyl as defined attached through a sulfinyl bridge (i.e. —S(=O)alkyl).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing a amino group with a hydroxyl group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

Experimental

Activity Assay for Nox2

Nox2 activity assay for primary screening: Plasma membranes were prepared from human neutrophils, which express large amounts of Nox2, stored at −80 C until use. See Curnutte et al., J. Biol. Chem. 1987, 262, 6450-6452, hereby incorporated by reference. Membranes are mixed with recombinant, purified cytosolic regulatory proteins (p67Np47N chimera, and a constitutively active mutant of Rac, Rac1(Q61)) and FAD, along with varying concentrations of compound, and LO12, which emits light when it reacts with ROS. The reaction is initiated by addition of NADPH and SDS (an artificial activator of Nox2).

Nox2 assay in human neutrophils: Human neutrophils were obtained from healthy volunteers (REF). LO12 luminescence was quantified as above. Nox4 assay using stably transfected HEK cell: HEK cells stably transfected with human Nox4 were incubated with varying concentrations of compound along with LO12.

Nox4 produces hydrogen peroxide rather than superoxide; under these conditions LO12 luminesces only after the addition of horseradish peroxidase to initiate the reaction.

Assay controls. To rule out interference with either Nox2 or Nox4 luminescence assays, two approaches are used. In one, xanthine oxidase replaces the Nox2 enzymatic system as the source of ROS in the Nox2/LO12 assay. Xanthine is added to initiate the reaction and LO12 luminescence is recorded. In the other, exogenous $H_2O_2$ is supplied in place of the Nox4 expressing $H_2O_2$-generating cells and luminescence is recorded.

2-((4-acetylphenyl)amino)-1-(4-(4-methoxyphenyl) piperazin-1-yl)ethanone (TG2-150) and Analogs

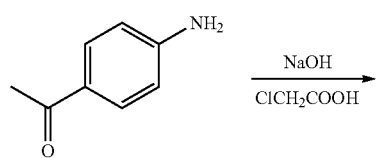

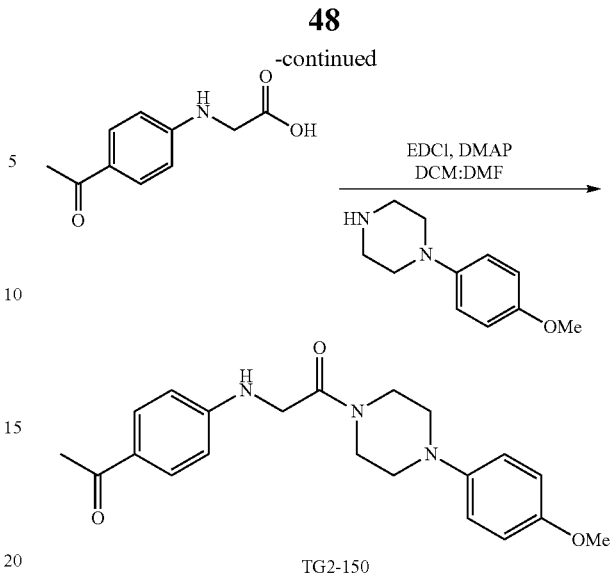

TG2-150

Chloroacetic acid (40 mmol) was neutralized with aqueous 2N NaOH (50 mmol), then 4-aminoacetophenone was added (25 mmol) was added to the above solution, and the whole reaction mixture was refluxed for 5 hrs. Cooled the reaction mixture, and the solid separated was filtered and washed with water. The solid was recrystallized from aqueous ethanol to get pure 2-((4-acetylphenyl)amino)acetic acid (4.2 g, 90% yield). To a solution of 1-(4-methoxyphenyl) piperazine (0.6 mmol) and 2-((4-acetylphenyl)amino)acetic acid (0.66 mmol) (obtained from the above reaction step) and DMAP (cat) in dichloromethane was added EDCI (0.8 mmol), and the resulting reaction mixture was stirred for 8 h. The reaction mixture was diluted with ethyl acetate and washed with dilute HCl solution, saturated NaHCO3 solution, water and brine solution. Dried the solution with sodium sulfate and concentrated to give crude mass which on silica gel chromatography eluting with 0.6% methanol in dichloromethane provided TG2-150 (70% yield). Similar synthetic procedures were used for making the compounds listed in Table 1 and Table 2.

TG2-150: $^1$H NMR (400 MHz, CDCl$_3$) δ 7.83 (d, J=8.8 Hz, 2H), 6.8 (m, 4H), 6.56 (d, J=8.8 Hz, 2H), 5.5 (t, 1H), 3.97 (d, J=4 Hz, 2H), 3.84 (t, J=4.8 Hz, 2H), 3.76 (s, 3H), 3.60 (t, J=4.8 Hz, 2H), 3.08 (m, 4H), 2.49 (s, 3H). LCMS. Cacld. for $C_{21}H_{25}N_3O_3$ (M+H) 368. found 368.

TG6-161: $^1$H NMR (400 MHz, CDCl$_3$+MeOH-d$_4$) δ 9.4 (s, 1H), 8.3 (s, 1H), 7.94 (dd, J=8.8, 1.6 Hz, 1H), 7.44 (d, J=8.8 Hz, 1H), 6.92 (m, 5H), 4.0 (m, 4H), 3.76 (s, 3H), 3.16 (t, J=5.2 Hz, 4H), 2.65 (s, 3H). Anal. Calcd for $C_{22}H_{23}N_3O_3$: C, 70.0; H, 6.14; N, 11.13. Found: C, 69.23; H, 6.08; N, 10.95. LCMS. Cacld. 378 (M+H). found 378.

TG6-179-3: $^1$H NMR (400 MHz, CDCl$_3$) δ 11.6 (bs, 1H), 7.46 (m, 1H), 7.19-7.0 (m, 2H), 6.94 (m, 2H), 6.85 (m, 2H), 4.96 (t, J=4.8 Hz, 2H), 4.06 (t, J=4.8 Hz, 2H), 3.76 (s, 3H), 3.21 (t, J=5.2 Hz, 4H). Anal. Calcd for $C_{19}H_{19}FN_4O_2$: C, 64.40; H, 5.40; N, 15.81. Found: C, 64.28; H, 5.55; N, 15.58. LCMS. Cacld. 355 (M+H). found 355.

The synthesis of the TG2-150 is shown above, which provides the basis for the synthesis of other analogs. Analogs with modifications at different regions of the molecule are shown in Table 1.

TABLE 1

Structure

| entry | Compound ID | IC$_{50}$ (μM) Nox 2 | IC$_{50}$ (μM) XO |
|---|---|---|---|
| 1 | TG2-150# | 0.4 | >20 |
| 2 | TG6-140# | 0.6 | >20 |
| 3 | TG6-149 | 0.8 | >20 |
| 4 | TG6-153 | 0.5 | >20 |
| 5 | TG6-158 | 0.6 | >20 |
| 6 | TG6-167-2 | 1.0 | NT |

TABLE 1-continued

| entry | Compound ID | Structure | IC$_{50}$ (µM) Nox 2 | XO |
|---|---|---|---|---|
| 7 | TG6-116-1 | | Not active | NT |
| 8 | TG6-116-2 | | Not active | NT |
| 9 | TG6-117-1 | | Not active | NT |
| 10 | TG6-117-2 | | Not active | NT |
| 11 | TG6-119-1 | | Not active | NT |
| 12 | TG6-119-2 | | Not active | NT |

TABLE 1-continued

| entry | Compound ID | Structure | IC$_{50}$ (µM) Nox 2 | XO |
|---|---|---|---|---|
| 13 | TG6-124 | | Not active | NT |
| 14 | TG6-128-1 | | Not active | NT |
| 15 | TG6-128-2 | | Not active | NT |
| 16 | TG6-130 | | Not active | NT |

TABLE 1-continued

| entry | Compound ID | Structure | IC$_{50}$ (µM) Nox 2 | XO |
|---|---|---|---|---|
| 17 | TG6-143-2 | | 1 | >20 |
| 18 | TG6-144-2 | | 0.2 | 0.2 |
| 19 | TG6-146-1 | | Not active | NT |
| 20 | TG6-146-2 | | Not active | NT |

TABLE 1-continued

| entry | Compound ID | Structure | IC$_{50}$ (μM) Nox 2 | XO |
|---|---|---|---|---|
| 21 | TG6-167-1 | (4-fluorophenyl)amino-acetyl-piperazine-(4-methoxyphenyl) | 3 | NT |
| 22 | TG6-169 | (2-fluorophenyl)amino-acetyl-piperazine-(4-methoxyphenyl) | 4.5 | NT |
| 23 | TG6-197 | (4-acetylphenyl)amino-acetyl-piperazine-(3,4-dimethoxyphenyl) | 1.3 | NT |
| 24 | TG2-160-2 | (4-acetylphenyl)amino-acetyl-piperazine-(3-chlorophenyl) | Not active | NT |
| 25 | TG2-163 | (4-acetylphenyl)amino-acetyl-piperazine-(4-trifluoromethylphenyl) | Not active | NT |
| 26 | TG2-165-2 | (4-isopropylphenyl)amino-acetyl-piperazine-(4-trifluoromethylphenyl) | Not active | NT |

TABLE 1-continued

Structure

| entry | Compound ID | IC$_{50}$ (µM) Nox 2 | XO |
|---|---|---|---|
| 27 | TG2-171-1 | 0.5 | 0.2 |
| 28 | TG2-171-2 | 10 (50%) | NT |
| 29 | TG2-181-1 | 4 | 20 |
| 30 | TG2-181-2 | Not active | NT |
| 31 | TG6-120-4 | 0.1 | 0.2 |

TABLE 1-continued

| entry | Compound ID | Structure | IC$_{50}$ (μM) Nox 2 | XO |
|---|---|---|---|---|
| 32 | TG2-158-2 | 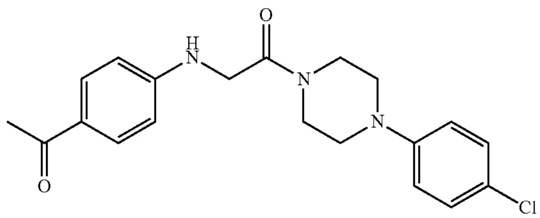 [SMILES: CC(=O)c1ccc(NCC(=O)N2CCN(c3ccc(Cl)cc3)CC2)cc1] | Not active | NT |
| 33 | TG6-205-1 | 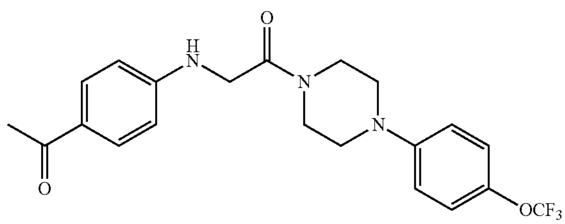 [SMILES: CC(=O)c1ccc(NCC(=O)N2CCN(c3ccc(OC(F)(F)F)cc3)CC2)cc1] | Not active | >20 |

The synthesis of additional analogs was achieved as exemplified in the scheme below, starting from 5-substituted indole-2-carboxylic acids, which in turn were procured from commercially available amines using a known method. Using similar synthetic methods, derivatives were prepared containing indole, imidazole and quinolin.

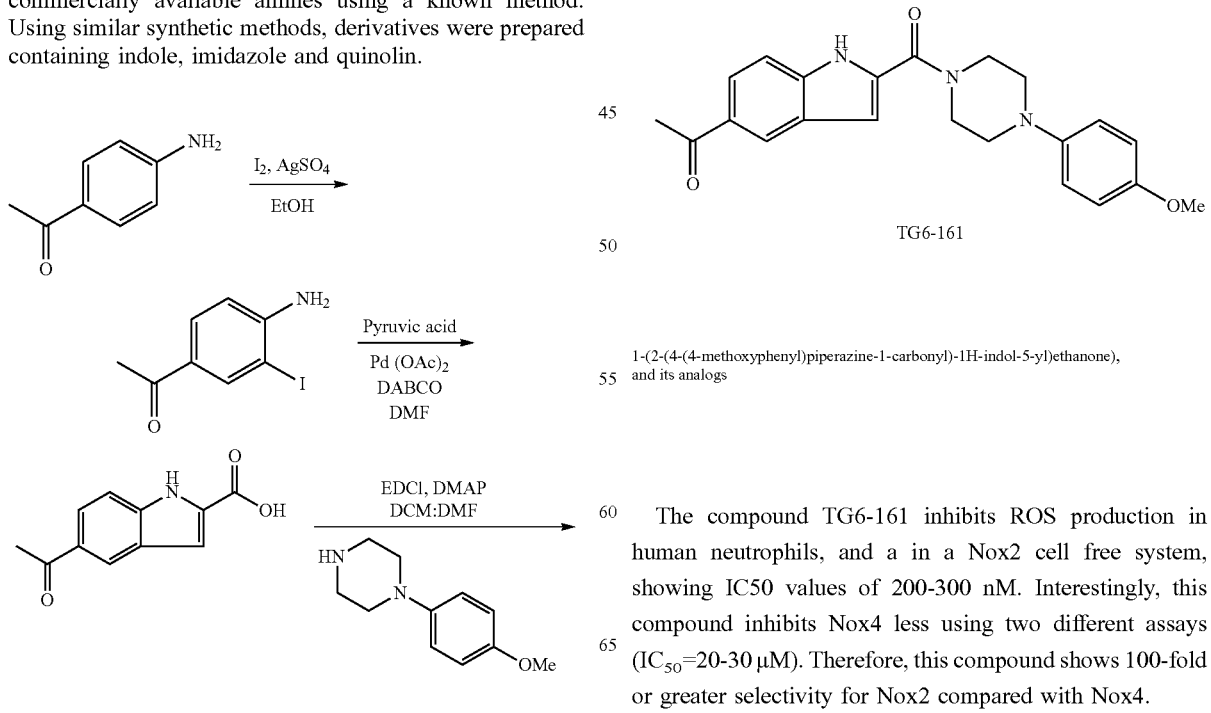

TG6-161

1-(2-(4-(4-methoxyphenyl)piperazine-1-carbonyl)-1H-indol-5-yl)ethanone), and its analogs The compound TG6-161 inhibits ROS production in human neutrophils, and a in a Nox2 cell free system, showing IC50 values of 200-300 nM. Interestingly, this compound inhibits Nox4 less using two different assays (IC$_{50}$=20-30 μM). Therefore, this compound shows 100-fold or greater selectivity for Nox2 compared with Nox4.

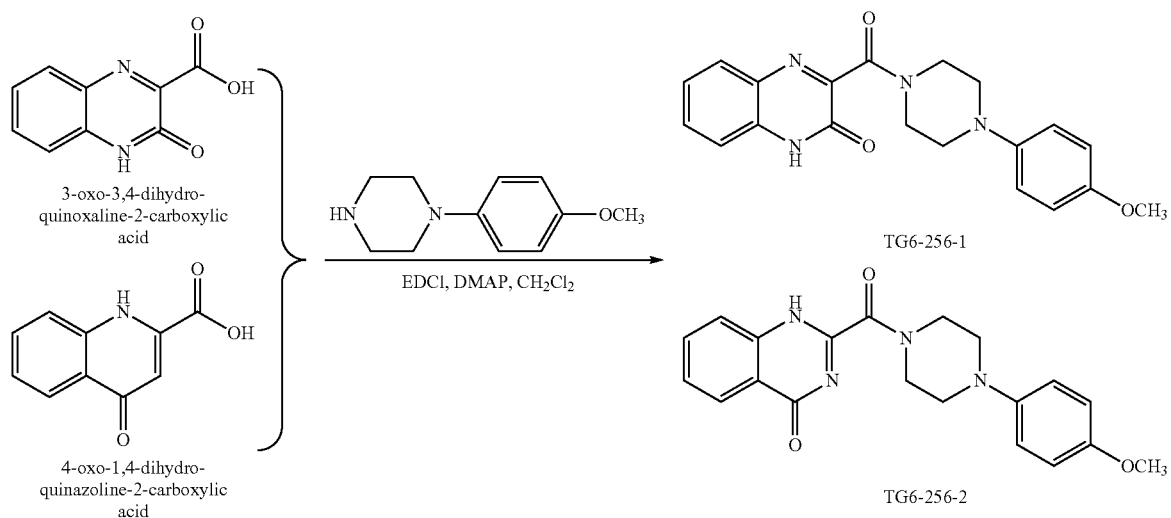
One prepares TG6-256-1, TG6-256-2 from commercially available starting materials 3-oxo-3,4-dihydro-quinoxaline-2-carboxylic acid and 4-oxo-1,4-dihydro-quinazoline-2-carboxylic acid by a carbodiimide coupling reaction in similar fashion to that of TG2-150.
TABLE 2
| entry | Compound | Structure | IC$_{50}$ (μM) Nox2 | XO |
|---|---|---|---|---|
| 1 | TG6-161 | 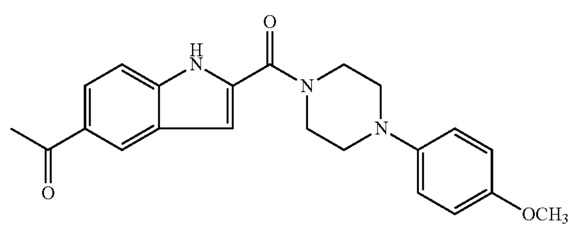 [SMILES: COc1ccc(N2CCN(C(=O)c3cc4cc(C(C)=O)ccc4[nH]3)CC2)cc1] | 0.4 | >20 |
| 2 | TG6-179-2 | 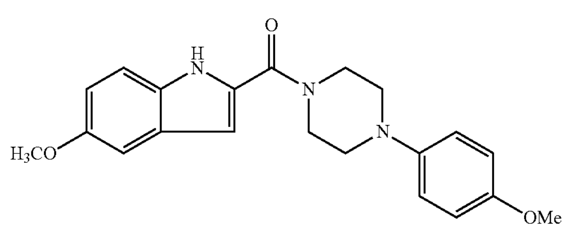 [SMILES: COc1ccc(N2CCN(C(=O)c3cc4cc(OC)ccc4[nH]3)CC2)cc1] | 0.5 | NT |
| 3 | TG6-179-3 | 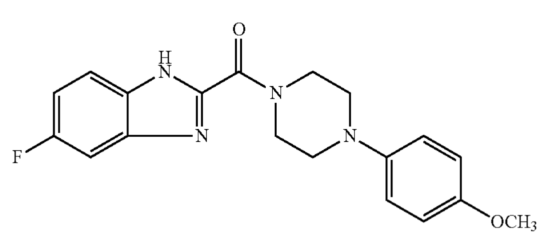 [SMILES: COc1ccc(N2CCN(C(=O)c3nc4cc(F)ccc4[nH]3)CC2)cc1] | 0.7 | >20 |

TABLE 2-continued

| entry | Compound | Structure | IC$_{50}$ (μM) Nox2 | IC$_{50}$ (μM) XO |
|---|---|---|---|---|
| 4 | TG6-181 | 5,6-dimethoxy-1H-indole-2-carbonyl-piperazine-N-(4-methoxyphenyl) | 0.8 | >20 |
| 5 | TG6-191 | 6-fluoro-4-hydroxyquinoline-3-carbonyl-piperazine-N-(4-methoxyphenyl) | 1.5 | NT |
| 6 | TG6-179-1 | 5-fluoro-1H-indole-2-carbonyl-piperazine-N-(4-methoxyphenyl) | 5 | NT |
| 7 | TG6-190 | 5-acetyl-3-methyl-1H-indole-2-carbonyl-piperazine-N-(4-methoxyphenyl) | 1 | NT |
| 8 | TG6-192 | 8-fluoro-4-hydroxyquinoline-3-carbonyl-piperazine-N-(4-methoxyphenyl) | Not active | NT |
| 9 | TG6-199 | 5-hydroxy-1H-indole-2-carbonyl-piperazine-N-(4-methoxyphenyl) | 0.5 | <0.1 |

TABLE 2-continued

| entry | Compound | Structure | IC$_{50}$ (μM) Nox2 | IC$_{50}$ (μM) XO |
|---|---|---|---|---|
| 10 | TG6-200 | 5-fluoro-3-methyl-1H-indole-2-carbonyl-piperazine-N-(4-methoxyphenyl) | 0.7 | NT |
| 11 | TG6-202 | 5-ethyl-1H-indole-2-carbonyl-piperazine-N-(4-methoxyphenyl) | Not active | >20 |
| 12 | TG6-203 | 5-bromo-1H-indole-2-carbonyl-piperazine-N-(4-methoxyphenyl) | 30% inhibition at 0.3 uM | NT |
| 13 | TG6-205-2 | 5-hydroxy-1H-indole-2-carbonyl-piperazine-N-(4-trifluoromethoxyphenyl) | 1.5 | 0.2 |
| 14 | TG6-206 | 5-fluoro-1H-benzimidazole-2-carbonyl-piperazine-N-(4-trifluoromethoxyphenyl) | Not active | NT |
| 15 | TG6-208 | 3-acetamido-5-methoxy-1H-indole-2-carbonyl-piperazine-N-(4-methoxyphenyl) | 60% inhibition at 2 uM | NT |

TABLE 2-continued

| entry | Compound | Structure | IC$_{50}$ (μM) Nox2 | XO |
|---|---|---|---|---|
| 16 | TG6-209 | 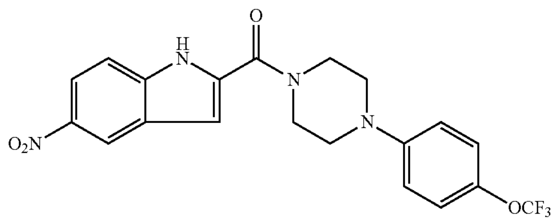 [SMILES: O=C(c1cc2cc([N+](=O)[O-])ccc2[nH]1)N1CCN(c2ccc(OC(F)(F)F)cc2)CC1] | 25% inhibition at 2 uM | NT |
| 17 | TG6-214 | 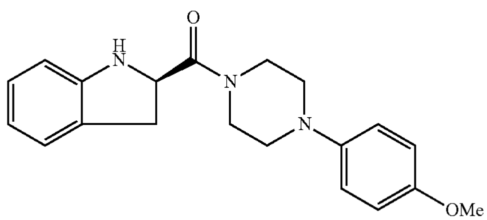 [SMILES: COc1ccc(N2CCN(C(=O)[C@H]3Cc4ccccc4N3)CC2)cc1] | 40% inhibition at 2.5 uM | NT |
| 18 | TG6-225 | 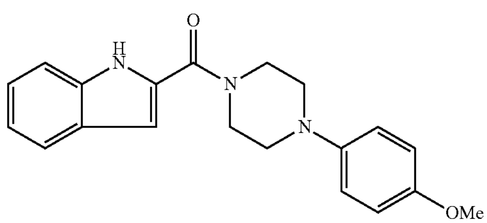 [SMILES: COc1ccc(N2CCN(C(=O)c3cc4ccccc4[nH]3)CC2)cc1] | 0.5 | >20 |
| 19 | TG6-218 | 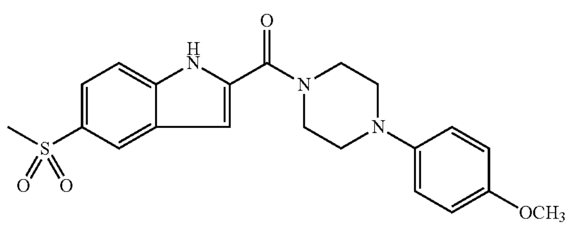 [SMILES: COc1ccc(N2CCN(C(=O)c3cc4cc(S(C)(=O)=O)ccc4[nH]3)CC2)cc1] | 40% inhibition at 6 uM | NT |
| 20 | TG6-222 | 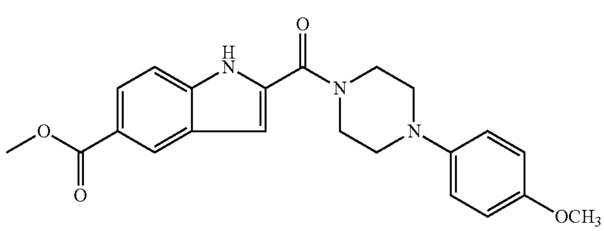 [SMILES: COC(=O)c1ccc2[nH]c(C(=O)N3CCN(c4ccc(OC)cc4)CC3)cc2c1] | 0.3 | >20 |
| 21 | TG6-223 | 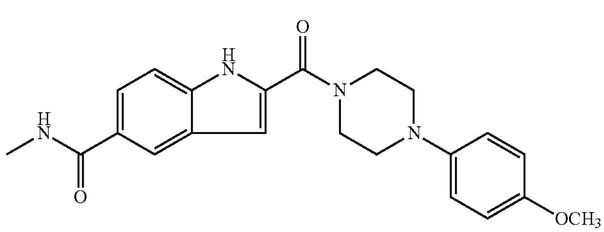 [SMILES: CNC(=O)c1ccc2[nH]c(C(=O)N3CCN(c4ccc(OC)cc4)CC3)cc2c1] | 0.5 | >20 |

TABLE 2-continued

| entry | Compound | Structure | IC$_{50}$ (μM) Nox2 | XO |
|---|---|---|---|---|
| 22 | TG6-227 | 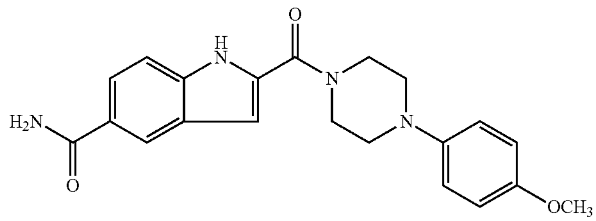 [SMILES: COc1ccc(N2CCN(C(=O)c3cc4cc(C(N)=O)ccc4[nH]3)CC2)cc1] | 0.7 | >20 |
| 23 | TG6-228 | | 1 | >20 |
| 24 | TG6-235 | | 1 | >20 |
| 23 | TG6-236 | | 0.5 | >20 |
| 24 | TG6-238 | | 0.8 | 20 |
| 25 | TG6-239 | 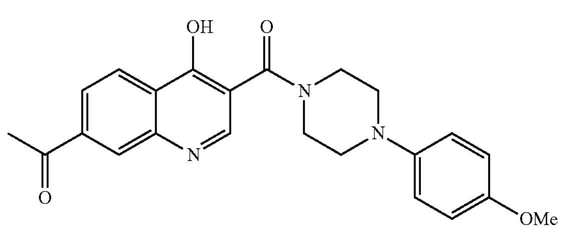 [SMILES: COc1ccc(N2CCN(C(=O)c3cnc4cc(C(C)=O)ccc4c3O)CC2)cc1] | 1 | 20 |

TABLE 2-continued

| entry | Compound | Structure | IC$_{50}$ (μM) Nox2 | IC$_{50}$ (μM) XO |
|---|---|---|---|---|
| 26 | TG6-242 | 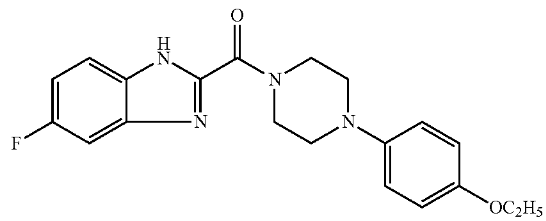 [SMILES: CCOc1ccc(N2CCN(C(=O)c3nc4cc(F)ccc4[nH]3)CC2)cc1] | 0.8 | NT |
| 27 | TG6-252 | 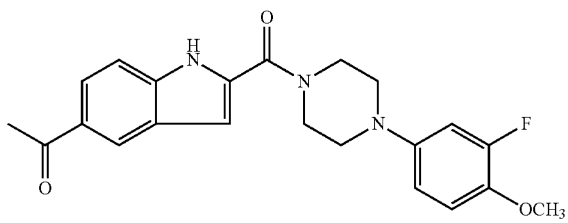 [SMILES: COc1ccc(N2CCN(C(=O)c3cc4cc(C(C)=O)ccc4[nH]3)CC2)cc1F] | 3 | NT |
| 28 | TG6-251-2 | 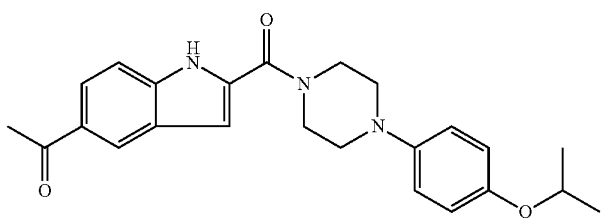 [SMILES: CC(=O)c1ccc2[nH]c(C(=O)N3CCN(c4ccc(OC(C)C)cc4)CC3)cc2c1] | 1 | NT |
| 29 | TG6-251-1 | 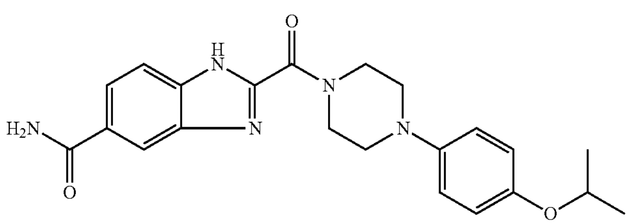 [SMILES: CC(C)Oc1ccc(N2CCN(C(=O)c3nc4cc(C(N)=O)ccc4[nH]3)CC2)cc1] | 1 | 20 |
| 30 | TG6-254-1 | 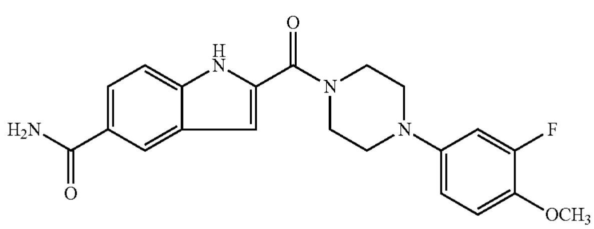 [SMILES: COc1ccc(N2CCN(C(=O)c3cc4cc(C(N)=O)ccc4[nH]3)CC2)cc1F] | 2 | NT |
| 31 | TG6-254-2 | 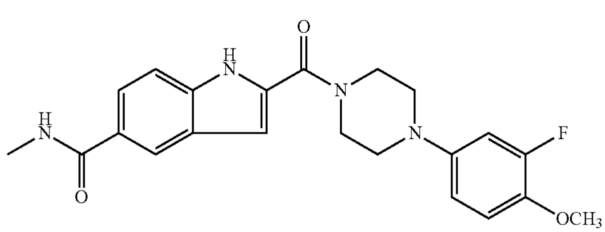 [SMILES: CNC(=O)c1ccc2[nH]c(C(=O)N3CCN(c4ccc(OC)c(F)c4)CC3)cc2c1] | 10 | NT |

TABLE 2-continued

| entry | Compound | Structure | IC$_{50}$ (µM) Nox2 | XO |
|---|---|---|---|---|
| 32 | TG6-256-1 | 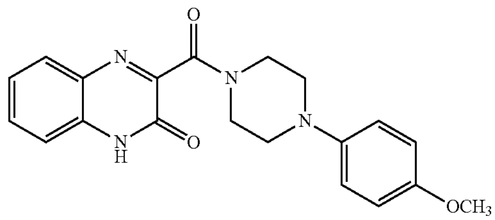 [SMILES: COc1ccc(N2CCN(C(=O)c3nc4ccccc4[nH]c3=O)CC2)cc1] | | |
| 33 | TG6-256-2 | 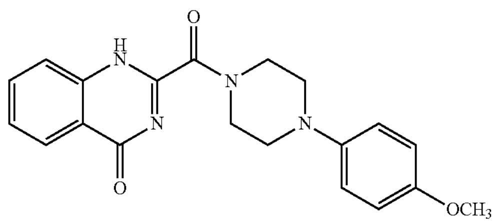 [SMILES: COc1ccc(N2CCN(C(=O)c3nc(=O)c4ccccc4[nH]3)CC2)cc1] | | |

(3-(((2-(diethylamino)ethyl)amino)methyl)-5-fluoro-1H-indol-2-yl)(4-(4-methoxyphenyl)piperazin-1-yl)methanone (TG6-298) and Analogs

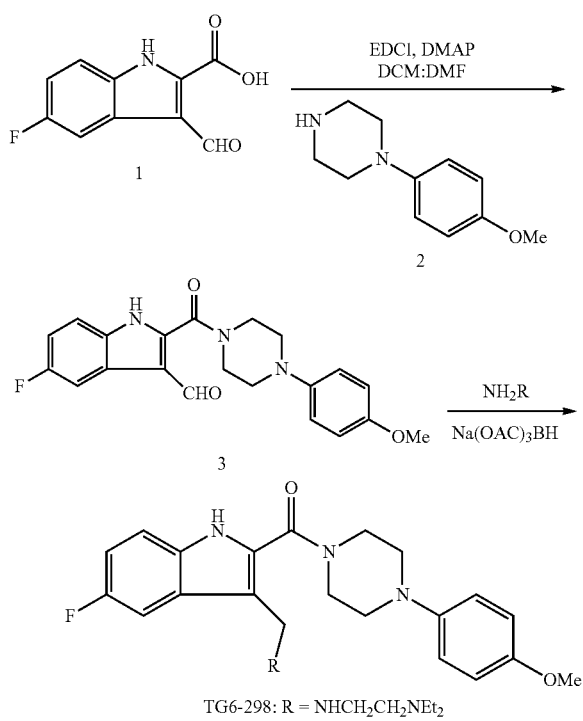

To a solution of acid 1 (100 mg, 1 eq) and piperazine 2 (92 mg, 1 eq) in dichloromethane and N,N-dimethylformamide mixture (10:1) (6 ml), was added dimethylaminopyridine (DMAP) (5 mg) and ethyl-3-(3-dimethylaminopropyl)carbodiimide.hydrochloride (EDCI) (120 mg, 0.63, 1.3 eq) and resulting reaction as stirred at room temperature for 8 hrs. The reaction was quenched with addition of water, followed by ethyl acetate. Organics were subjected to acid, and base work gave to get crude mass, which on recrystallization with methanol gave pure product 3 (110 mg, 60% yield). 3: $^1$H NMR (400 MHz, CDCl$_3$): δ 12.8 (bs, 1H), 10.0 (s, CHO), 7.90 (dd, J=9.4, 2.8 Hz, 1H), 7.50 (dd, J=8.8, 4.4 Hz, 1H), 7.16 (t x d, J=8.8, 2.4 Hz, 1H), 6.89 (d, J=9.2 Hz, 2H), 6.80 (d, J=8.8 Hz, 2H), 3.82 (bs, 2H), 3.46 (bs, 2H), 3.10 (bs, 2H), 2.96 (bs, 2H). LCMS: Calcd. for C$_{21}$H$_{21}$FN$_3$O$_3$ (M+H) 382. found 382.

Step-2:

To the solution of 3 (70 mg, 0.18 mmol, 1 eq), N,N-diethylethylenediamine (51 uL, 2 eq) in dichloromethane (8 ml) was added sodium triacetoxyborohydride (116 mg, 0.5 mmol, 3 eq), and acetic acid (0.024 ml, 2 eq) at room temperature, and the resulting reaction mixture was stirred overnight. 1N NaOH was added to quench the reaction and product was extracted with ethyl acetate, dried and concentrated to give crude, which on silica gel chromatography provided product TG6-298. Similar procedure was employed to prepare other compounds in this class (see Table 3).

TG6-298: $^1$H NMR (400 MHz, CDCl$_3$): δ 7.40 (m, 1H), 7.2 (m, 1H), 6.90 (m, 1H), 6.80 (m, 4H), 3.93 (s, 2H), 3.8 (bs, 4H), 3.73 (s, 3H), 3.02 (bs, 4H), 2.52 (m, 2H), 2.45 (q, J=7 Hz, 4H), 0.93 (t, J=7 Hz, 6H). LCMS: Calcd. for C$_{27}$H$_{37}$FN$_5$O$_2$ (M+H) 482. found 482.

TG7-31: $^1$H NMR (400 MHz, CDCl$_3$): δ 9.9 (s, NH), 7.46 (dd, J=10, 2.4 Hz, 1H), 7.19 (dd, J=8.8, 4.4 Hz, 1H), 6.93 (t x d, J=8.8, 2.4 Hz, 1H), 1H), 6.83 (m, 4H), 3.76 (bs, 4H), 3.74 (s, 3H), 3.65 (s, 2H), 3.63 (m, 4H), 3.0 (bs, 4H), 2.40 (bs, 4H). LCMS: Calcd. for C$_{25}$H$_{30}$FN$_4$O$_3$ (M+H) 453. found 453.

TG7-32: $^1$H NMR (400 MHz, CDCl$_3$): δ 9.6 (s, NH), 7.3 (dd, J=10, 2.4 Hz, 1H), 7.20 (m, 2H), 6.93 (t x d, J=8.8, 2.4 Hz, 1H), 1H), 6.81 (m, 4H), 3.92 (s, 2H), 3.78 (bs, 4H), 3.73 (s, 3H), 3.60 (bs, 1H), 3.0 (bs, 4H), 2.92 (bs, 1H), 2.76 (bs, 2H), 2.2 (s, 3H), 1.98 (m, 2H), 1.90 (m, 2H). LCMS: Calcd. for C$_{27}$H$_{35}$FN$_5$O$_2$ (M+H) 480. found 480.

TG7-33: $^1$H NMR (400 MHz, CDCl$_3$): δ 9.4 (s, NH), 7.45 (dd, J=10, 2.4 Hz, 1H), 7.21 (dd, J=8.8, 4.4 Hz, 1H), 6.94 (t x d, J=8.8, 2.4 Hz, 1H), 6.83 (m, 4H), 3.78 (bs, 4H), 3.74 (s, 3H), 3.67 (s, 2H), 3.0 (bs, 4H), 2.40 (bs, 6H), 2.36 (q, J=7

Hz, 2H), 2.0 (s, 2H), 1.0 (t, J=7 Hz, 3H). LCMS: Calcd. for C$_{27}$H$_{35}$FN$_5$O$_2$ (M+H) 480. found 480.

TG7-34: $^1$H NMR (400 MHz, CDCl$_3$): δ 9.58 (s, NH), 7.51 (dd, J=10, 2.4 Hz, 1H), 7.21 (dd, J=8.8, 4.4 Hz, 1H), 6.94 (t x d, J=8.8, 2.4 Hz, 1H), 6.83 (m, 4H), 3.79 (bs, 4H), 3.74 (s, 3H), 3.70 (s, 2H), 3.0 (bs, 4H), 2.46 (q, J=7 Hz, 4H), 0.99 (t, J=7 Hz, 6H).

LCMS: Calcd. for C$_{25}$H$_{32}$FN$_5$O$_2$ (M+H) 439. found 439.

TABLE 3

| Compound | Structure | Nox2 (Cell Free) (μM) | Nox2 (PMN) (μM) | Nox1 (μM) | Nox5 (μM) | Solubility (μM) | Stability in liver S9-fractions (t ½) | | |
|---|---|---|---|---|---|---|---|---|---|
| | | | | | | | Mouse | Dog | Human |
| TG6-161 | 5-acetyl-1H-indole-2-carbonyl-piperazine-(4-methoxyphenyl) | 0.3 | 0.2 | 0.6 | ND | <25 μM | 3 h | 2 h | 45 min |
| TG6-179-3 | 5-fluoro-1H-benzimidazole-2-carbonyl-piperazine-(4-methoxyphenyl) | 1 | 0.4 | 0.6 | ND | <25 μM | 5 h | 4 h | 1 h |
| TG6-227 | 5-carbamoyl-1H-indole-2-carbonyl-piperazine-(4-methoxyphenyl) | 0.6 | 0.1 | 0.3 | ND | 190 μM | 6 h | 4.5 h | 2 h |
| TG6-225 | 1H-indole-2-carbonyl-piperazine-(4-methoxyphenyl) | 0.4 | 0.2 | 0.5 | ND | <25 μM | 5 h | 2.5 h | 4.2 h |
| TG6-298 | 5-fluoro-3-((2-(diethylamino)ethylamino)methyl)-1H-indole-2-carbonyl-piperazine-(4-methoxyphenyl) ·2HCl | 0.3 | 0.2 | 0.9 | ND | 150 μM | ND | ND | ND |

TABLE 3-continued

| Compound | Structure | Nox2 (Cell Free) (μM) | Nox2 (PMN) (μM) | Nox1 (μM) | Nox5 (μM) | Solubility (μM) | Stability in liver S9-fractions (t ½) | | |
|---|---|---|---|---|---|---|---|---|---|
| | | | | | | | Mouse | Dog | Human |
| TG7-31 | (structure) HCl | 0.8 | 0.2 | 0.6 | 1.5 | 276 μM | ND | ND | ND |
| TG7-32 | (structure) 2HCl | 0.7 | 0.2 | 0.5 | 0.6 | 250 μM | ND | ND | ND |
| TG7-33 | (structure) 2HCl | 0.8 | 0.7 | 0.4 | 0.8 | 250 μM | ND | ND | ND |
| TG7-34 | (structure) HCl | 0.7 | 0.5 | 0.6 | 0.6 | 270 μM | ND | ND | ND |

TG6-161 and TG6-179-3 were non toxic to HEK and C6g cells up until 500 μM. TG6-161 was active against only two enzymes Mao-A, UDP-Glucuronyltransferase (UGT1A1) /~40 tested, and TG6-179-3 was only active against UGT1A1 enzyme /~40 tested.
*ND = Not determined

What is claimed:

1. A pharmaceutical composition comprising a compound of Formula IE,

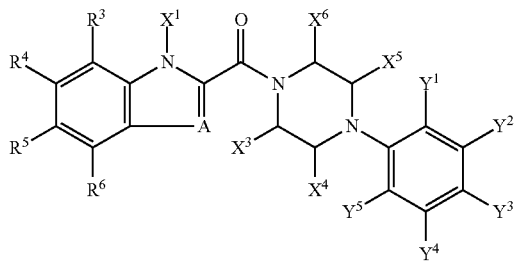

Formula IE or pharmaceutically acceptable salt thereof, wherein;
A is $CR^9$;
$R^9$ is hydrogen, or alkyl;
$Y^3$ is methoxy, ethoxy, trifluoromethoxy, isopropoxy, or alkoxy;
$Y^1$, $Y^2$, $Y^4$ and $Y^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl;
$R^3$, $R^4$, and $R^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl;
$R^5$ is alkylsulfonyl, alkoxycarbonyl, alkylcarbamoyl, alkanoyl, carboxy, or carbamoyl;
$X^1$ is hydrogen;
$X^3$, $X^4$, $X^5$, and $X^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl.

2. The composition of claim 1 wherein the compound is selected from the group consisting of:
 1-(2-(4-(4-methoxyphenyl)piperazine-1-carbonyl)-1H-indol-5-yl)ethanone;
 1-(2-(4-(4-methoxyphenyl)piperazine-1-carbonyl)-3-methyl-1H-indol-5-yl)ethanone;
 (4-(4-methoxyphenyl)piperazin-1-yl)(5-(methylsulfonyl)-1H-indol-2-yl)methanone;
 methyl 2-(4-(4-methoxyphenyl)piperazine-1-carbonyl)-1H-indole-5-carboxylate;
 2-(4-(4-methoxyphenyl)piperazine-1-carbonyl)-N-methyl-1H-indole-5-carboxamide;
 2-(4-(4-methoxyphenyl)piperazine-1-carbonyl)-1H-indole-5-carboxamide;
 2-(4-(4-methoxyphenyl)piperazine-1-carbonyl)-1H-indole-5-carboxylic acid;
 1-(2-(4-(4-ethoxyphenyl)piperazine-1-carbonyl)-1H-indol-5-yl)ethanone;
 1-(2-(4-(3-fluoro-4-methoxyphenyl)piperazine-1-carbonyl)-1H-indol-5-yl)ethanone; and
 1-(2-(4-(4-isopropoxyphenyl)piperazine-1-carbonyl)-1H-indol-5-yl)ethanone;
or salt thereof.

3. A pharmaceutical composition comprising a compound comprising Formula IIB,

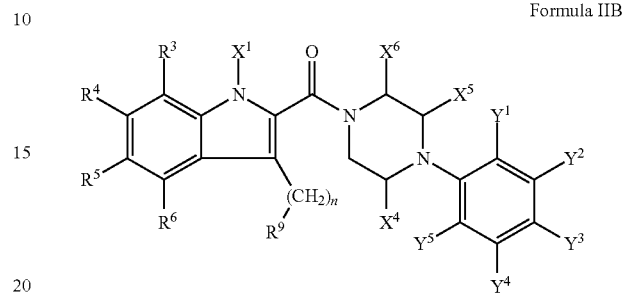

Formula IIB or pharmaceutically acceptable salt thereof, wherein;
n is 1 or 2;
$R^3$, $R^4$, $R^5$, and $R^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl;
$R^9$ is amino, alkylamino, dialkylamino, piperidinyl, piperazinyl, or morpholinyl wherein $R^9$ is optionally substituted with alkyl or dialkylamino;
$X^1$, $X^4$, $X^5$, and $X^6$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl;
$Y^1$, $Y^2$, $Y^3$, $Y^4$, and $Y^5$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, or aryl.

4. A pharmaceutical composition comprising a compound selected from the group consisting of:
 (3-(((2-(diethylamino)ethyl)amino)methyl)-5-fluoro-1H-indol-2-yl)(4-(4-methoxyphenyl)piperazin-1-yl)methanone;
 (5-fluoro-3-(morpholinomethyl)-1H-indol-2-yl)(4-(4-methoxyphenyl)piperazin-1-yl)methanone;
 (5-fluoro-3-(((1-methylpiperidin-4-yl)amino)methyl)-1H-indol-2-yl)(4-(4-methoxyphenyl)piperazin-1-yl)methanone;
 (3-((4-ethylpiperazin-1-yl)methyl)-5-fluoro-1H-indol-2-yl)(4-(4-methoxyphenyl)piperazin-1-yl)methanone; and
 (3-((diethylamino)methyl)-5-fluoro-1H-indol-2-yl)(4-(4-methoxyphenyl)piperazin-1-yl)methanone
or salts thereof.

* * * * *